(12) United States Patent
Nuccitelli et al.

(10) Patent No.: US 10,695,127 B2
(45) Date of Patent: Jun. 30, 2020

(54) NANOELECTROABLATION CONTROL AND VACCINATION

(71) Applicant: Pulse Biosciences, Inc., Hayward, CA (US)

(72) Inventors: Richard Lee Nuccitelli, Millbrae, CA (US); Jon Casey Berridge, Oakland, CA (US); Zachary Mallon, San Francisco, CA (US); Mark Kreis, San Francisco, CA (US); Brian Athos, San Francisco, CA (US); Pamela Nuccitelli, Millbrae, CA (US)

(73) Assignee: PULSE BIOSCIENCES, INC., Hayward, CA (US)

( * ) Notice: Subject to any disclaimer, the term of this patent is extended or adjusted under 35 U.S.C. 154(b) by 0 days.

(21) Appl. No.: 16/384,676

(22) Filed: Apr. 15, 2019

(65) Prior Publication Data

US 2019/0239949 A1    Aug. 8, 2019

Related U.S. Application Data

(60) Continuation of application No. 16/040,434, filed on Jul. 19, 2018, now Pat. No. 10,307,207, which is a
(Continued)

(51) Int. Cl.
*A61B 18/14* (2006.01)
*A61N 1/40* (2006.01)
(Continued)

(52) U.S. Cl.
CPC ...... *A61B 18/1492* (2013.01); *A61B 1/00009* (2013.01); *A61B 1/00045* (2013.01);
(Continued)

(58) Field of Classification Search
CPC ....... A61B 18/1492; A61B 1/05; A61B 1/043; A61B 1/00045; A61B 1/00009;
(Continued)

(56) References Cited

U.S. PATENT DOCUMENTS 5,568,035 A    10/1996    Kato et al.
5,635,776 A    6/1997     Imi
(Continued)

FOREIGN PATENT DOCUMENTS

EP    1 900 375 A1    3/2008
JP    2013-223115 A    10/2013
(Continued)

OTHER PUBLICATIONS

NIH (National Institute of Health's National Cancer Institute, https://www.cancer.gov/publications/dictionaries/cancer-drug/def/autologous-tumor-cell-vaccine).*
(Continued)

*Primary Examiner* — Christopher Koharski
*Assistant Examiner* — James Moss
(74) *Attorney, Agent, or Firm* — Kilpatrick Townsend & Stockton LLP

(57) ABSTRACT

Techniques for treating a tumor and vaccinating against cancer are described. The techniques include treating the tumor by positioning electrodes over an interface between the tumor and non-tumor tissue and applying sub-microsecond pulsed electric fields. The positioning is facilitated by an imaginary contour line of a threshold value of the electric field. In an example, the imaginary contour line is overlaid over images that include the tumor such that the electrodes are properly positioned over the tumor. The techniques also include vaccinating against cancer by passing sub-microsecond pulsed electric fields through tumor cells of a subject sufficient to cause the tumor cells to express calreticulin on
(Continued)

surface membranes. The tumor cells are extracted and introduced with the expressed calreticulin into the subject or another subject, thereby providing a vaccination.

20 Claims, 22 Drawing Sheets

Related U.S. Application Data continuation of application No. 15/671,014, filed on Aug. 7, 2017, now Pat. No. 10,058,383, which is a division of application No. 14/954,630, filed on Nov. 30, 2015, now Pat. No. 9,724,155.

(60) Provisional application No. 62/086,025, filed on Dec. 1, 2014.

(51) Int. Cl.
| | | |
|---|---|---|
| *A61B 90/00* | (2016.01) | |
| *A61B 34/20* | (2016.01) | |
| *A61B 1/00* | (2006.01) | |
| *A61B 1/04* | (2006.01) | |
| *A61B 1/05* | (2006.01) | |
| *A61N 1/32* | (2006.01) | |
| *A61B 6/12* | (2006.01) | |
| *A61B 18/00* | (2006.01) | |
| *A61B 34/10* | (2016.01) | |
| *A61B 1/06* | (2006.01) | |
| *A61B 6/03* | (2006.01) | |
| *A61M 37/00* | (2006.01) | |

(52) U.S. Cl.
CPC ............... *A61B 1/04* (2013.01); *A61B 1/043* (2013.01); *A61B 1/05* (2013.01); *A61B 18/1477* (2013.01); *A61B 34/20* (2016.02); *A61B 90/37* (2016.02); *A61N 1/326* (2013.01); *A61N 1/40* (2013.01); *A61B 1/06* (2013.01); *A61B 6/03* (2013.01); *A61B 6/12* (2013.01); *A61B 2018/00273* (2013.01); *A61B 2018/00529* (2013.01); *A61B 2018/00577* (2013.01); *A61B 2018/00613* (2013.01); *A61B 2018/00642* (2013.01); *A61B 2018/00892* (2013.01); *A61B 2018/00904* (2013.01); *A61B 2018/00982* (2013.01); *A61B 2034/101* (2016.02); *A61B 2034/107* (2016.02); *A61M 2037/0007* (2013.01)

(58) Field of Classification Search
CPC ..... A61B 34/20; A61B 90/37; A61B 18/1477; A61B 1/04; A61B 1/06; A61B 2034/107; A61B 2034/101; A61B 2018/00613; A61B 6/12; A61B 2018/00982; A61B 2018/00904; A61B 2018/00892; A61B 2018/00642; A61B 2018/00577; A61B 2018/00529; A61B 2018/00273; A61B 6/03; A61N 1/40; A61N 1/326; A61M 2037/0007
See application file for complete search history.

(56) References Cited

U.S. PATENT DOCUMENTS

| | | |
|---|---|---|
| 5,774,348 A | 6/1998 | Druce et al. |
| 5,907,484 A | 5/1999 | Kowshik et al. |
| 6,008,690 A | 12/1999 | Takeshima et al. |
| 6,026,003 A | 2/2000 | Moore et al. |
| 6,048,789 A | 4/2000 | Vines et al. |
| 6,137,276 A | 10/2000 | Rudolph |
| 6,278,895 B1 | 8/2001 | Bernard |
| 6,326,177 B1 | 12/2001 | Schoenbach et al. |
| 6,426,666 B1 | 7/2002 | Li et al. |
| 6,831,377 B2 | 12/2004 | Yampolsky et al. |
| 7,483,738 B2 | 1/2009 | Tamarkin et al. |
| 7,496,401 B2 | 2/2009 | Bernabei |
| 7,565,201 B2 | 7/2009 | Blackmore |
| 7,615,357 B2 | 11/2009 | Maher et al. |
| 7,655,004 B2 | 2/2010 | Long |
| 7,767,433 B2 | 8/2010 | Kuthi et al. |
| 7,824,870 B2 | 11/2010 | Kovalcheck et al. |
| 7,855,904 B2 | 12/2010 | Kirbie et al. |
| 7,901,929 B2 | 3/2011 | Kuthi |
| 7,901,930 B2 | 3/2011 | Kuthi |
| 7,937,143 B2 | 5/2011 | Demarais et al. |
| 8,000,813 B2 | 8/2011 | Schoenbach et al. |
| 8,115,343 B2 | 2/2012 | Sanders |
| 8,120,207 B2 | 2/2012 | Sanders |
| 8,139,339 B2 | 3/2012 | Pakhomov |
| 8,506,564 B2 | 8/2013 | Long et al. |
| 8,512,334 B2 | 8/2013 | Nuccitelli |
| 8,682,426 B2 | 3/2014 | Schoenbach |
| 8,688,227 B2 | 4/2014 | Nuccitelli et al. |
| 8,709,006 B2 | 4/2014 | Juergen |
| 8,798,705 B2 | 8/2014 | Kolb |
| 8,822,222 B2 | 9/2014 | Beebe et al. |
| 8,926,606 B2 | 1/2015 | Davalos et al. |
| 8,948,878 B2 | 2/2015 | Schoenbach |
| 9,101,764 B2 | 8/2015 | Nuccitelli et al. |
| 9,724,155 B2 | 8/2017 | Nuccitelli et al. |
| 10,058,383 B2 | 8/2018 | Nuccitelli et al. |
| 10,137,152 B2 | 11/2018 | Nuccitelli et al. |
| 2001/0025177 A1 | 9/2001 | Woloszko et al. |
| 2002/0010491 A1 | 1/2002 | Schoenbach et al. |
| 2002/0146396 A1 | 10/2002 | Albert et al. |
| 2004/0080964 A1 | 4/2004 | Buchmann |
| 2004/0219056 A1 | 11/2004 | Tribelsky et al. |
| 2004/0240241 A1 | 12/2004 | Chueh et al. |
| 2005/0218423 A1 | 10/2005 | Shimizu et al. |
| 2005/0261672 A1 | 11/2005 | Deem et al. |
| 2006/0062074 A1 | 3/2006 | Gundersen et al. |
| 2006/0079886 A1 | 4/2006 | Orszulak et al. |
| 2006/0090723 A1 | 5/2006 | Stuart |
| 2006/0139977 A1 | 6/2006 | Oicles et al. |
| 2006/0216690 A1 | 9/2006 | Maher et al. |
| 2006/0269531 A1 | 11/2006 | Beebe |
| 2006/0281069 A1 | 12/2006 | Maher et al. |
| 2007/0031959 A1 | 2/2007 | Kuthi et al. |
| 2007/0129626 A1 | 6/2007 | Mahesh et al. |
| 2008/0031337 A1 | 2/2008 | Krishnaswamy et al. |
| 2008/0071262 A1 | 3/2008 | Azure et al. |
| 2008/0200912 A1 | 8/2008 | Long |
| 2008/0231337 A1 | 9/2008 | Krishnaswamy |
| 2009/0062792 A1 | 3/2009 | Vakharia et al. |
| 2009/0062795 A1 | 3/2009 | Vakharia et al. |
| 2009/0198231 A1 | 8/2009 | Esser et al. |
| 2009/0299362 A1 | 12/2009 | Long et al. |
| 2009/0299417 A1 | 12/2009 | Schoenbach |
| 2010/0038971 A1 | 2/2010 | Sanders et al. |
| 2010/0042095 A1 | 2/2010 | Bigley et al. |
| 2010/0063496 A1 | 3/2010 | Trovato et al. |
| 2010/0130972 A1 | 5/2010 | Yambor et al. |
| 2010/0152725 A1 | 6/2010 | Pearson et al. |
| 2010/0222734 A1 | 9/2010 | Jayes et al. |
| 2010/0240995 A1 | 9/2010 | Nuccitelli |
| 2010/0256630 A1 | 10/2010 | Hamilton et al. |
| 2010/0261994 A1 | 10/2010 | Davalos et al. |
| 2010/0274327 A1 | 10/2010 | Carroll et al. |
| 2010/0278401 A1 | 11/2010 | Schoenbach |
| 2010/0318082 A1* | 12/2010 | Nuccitelli ............... A61B 18/14 606/41 |
| 2011/0015630 A1 | 1/2011 | Azure |
| 2011/0092973 A1 | 4/2011 | Nuccitelli |
| 2011/0106221 A1 | 5/2011 | Neal, II et al. |
| 2011/0118729 A1 | 5/2011 | Heeren et al. |
| 2011/0144641 A1 | 6/2011 | Dimalanta et al. |
| 2011/0270249 A1 | 11/2011 | Utley et al. |
| 2011/0288545 A1 | 11/2011 | Beebe |
| 2011/0318319 A1 | 12/2011 | Hargrave |

(56) References Cited

U.S. PATENT DOCUMENTS

| | | |
|---|---|---|
| 2012/0035511 A1 | 2/2012 | Schoenbach |
| 2012/0059255 A1 | 3/2012 | Paul et al. |
| 2012/0089209 A1 | 4/2012 | Schoenbach |
| 2012/0109122 A1 | 5/2012 | Arena et al. |
| 2012/0109263 A1 | 5/2012 | Kolb et al. |
| 2012/0277763 A1 | 11/2012 | Greenblatt et al. |
| 2012/0310230 A1 | 12/2012 | Willis et al. |
| 2012/0315704 A1 | 12/2012 | Beebe |
| 2013/0011438 A1 | 1/2013 | Bartunkova |
| 2013/0018441 A1 | 1/2013 | Childs |
| 2013/0041443 A1 | 2/2013 | Weissberg |
| 2013/0150935 A1 | 6/2013 | Weissberg et al. |
| 2013/0172884 A1 | 7/2013 | Schoenbach |
| 2013/0260435 A1 | 10/2013 | Pakhomova |
| 2013/0302409 A1 | 11/2013 | Fuchs et al. |
| 2013/0345697 A1 | 12/2013 | Garcia et al. |
| 2014/0046322 A1* | 2/2014 | Callas ............... A61B 18/14 606/41 |
| 2014/0081256 A1 | 3/2014 | Carmel et al. |
| 2014/0106430 A1 | 4/2014 | Hargrave |
| 2014/0222126 A1 | 8/2014 | Xiao |
| 2014/0358066 A1 | 12/2014 | Nuccitelli et al. |
| 2014/0364797 A1 | 12/2014 | Schoenbach |
| 2015/0201991 A1 | 7/2015 | Zemlin |
| 2015/0320999 A1 | 11/2015 | Nuccitelli et al. |
| 2017/0245928 A1 | 8/2017 | Xiao et al. |
| 2018/0078755 A1 | 3/2018 | Kreis et al. |
| 2019/0046791 A1 | 2/2019 | Ebbers et al. |
| 2019/0217080 A1 | 7/2019 | Moss et al. |

FOREIGN PATENT DOCUMENTS

| | | | |
|---|---|---|---|
| WO | 2010/011408 | A1 | 1/2010 |
| WO | 2014/060854 | A1 | 4/2014 |
| WO | 2014/133870 | A1 | 9/2014 |
| WO | 2014/197240 | A2 | 12/2014 |

OTHER PUBLICATIONS

Richard Nuccitelli et al., "Optimized nanosecond pulsed electric field therapy can cause murine malignant melanomas to self-destruct with a single treatment", Int. J. Cancer: 127, 1727-1736 (2010), https://onlinelibrary.wiley.com/doi/full/10.1002/ijc.25364, viewed on Oct. 15, 2019.*

S. J. Beebe et al., "Nanosecond pulsed electric field (nsPEF) effects on cells and tissues: apoptosis induction and tumor growth inhibition," in IEEE Transactions on Plasma Science, vol. 30, No. 1, pp. 286-292, Feb. 2002. doi: 10.1109/TPS.2002.1003872.*

Stephan R Scheffer et al., "Apoptotic, but not necrotic, tumor cell vaccines induce a potent immune response in vivo", published: 2003, https://doi.org/10.1002/ijc.10777, viewed on Oct. 16, 2019.*

Stephen Beebe et al., "Pulse Power Ablation of Melanoma with Nanosecond Pulsed Electric Fields", Treatment of Metastatic Melanoma, Ch. 11, Published: Oct. 5, 2011, https://doi.org/10.5772/22850, viewed on Oct. 16, 2019.*

Jeffrey Perkel, "Fluorescence-Activated Cell Sorter", Jul. 2004, https://www.the-scientist.com/how-it-works/fluorescence-activated-cell-sorter-49796, viewed on Oct. 17, 2019.*

PromoKine, "Apoptotic Cell Isolation Kit", https://www.promocell.com/f/2018/01/PK-CA577-K258.pdf, Jun. 2014, viewed on Oct. 17, 2019.*

Wei Ren et al., S.J. Apoptosis (2011) 16: 382. https://doi.org/10.1007/s10495-010-0572-y.*

Baker et al., "Stacking Power MOSFETs for use in High Speed Instrumentation," Rev. Sci. Instrum., American Institute of Physics, Dec. 1992, vol. 63, No. 12, pp. 5799-5801.

Barth R. F., "Rat brain tumor models in experimental neuro-oncology: The 9L, C6, T9, F98, RG2 (D47), RT-2 and CNS-1 Gliomas," J Neurooncol., 1998, 36(1): pp. 91-102.

Beebe et al., "Diverse Effects of Nanosecond Pulsed Electric Fields on Cells and Tissues," DNA and Cell Biology, 2003, vol. 22, No. 12, pp. 785-796.

Bhosale et al., "Design and Simulation of 50 kV, 50 A Solid State Marx Generator," International Conference on Magnetics, Machines & Drives (AICERA—2014 iCMMD), IEEE 2014, pp. 1-5.

Bier et al. 1999. Kinetics of Sealing for Transient Electropores in Isolated Mammalian Skeletal Muscle Cells, Bioelectromagnetics, vol. 20, pp. 194-201.

Borner et al. 1994, The detergent Triton X-100 induces a death pattern in human carcinoma cell lines that resembles cytotoxic lymphocyte-induced apoptosis. FEBS Lett. 353: pp. 129-132.

Calvet et al., "Electrochemotherapy with bleomycin induces hall-marks of immunogenic cell death in murine colon cancer cells," Oncoimmunology, Apr. 15, 2014, vol. 3, No. 4, 12 pages.

Carey et al., "Marx Generator Design and Performance," Applied Physical Electronics, L.C., 2002, 4 pages.

Casey et al., "Solid-State Marx Bank Modulator for the Next Generation Linear Collider," Conference Record of the 26$^{th}$ International Power Modulator Symposium and 2004 High Voltage Workshop (PMC), San Francisco, California, May 23-26, 2004, IEEE 2004, pp. 257-260.

Chen, X. et al., "Apoptosis initiation and angiogenesis inhibition: melanoma targets for nanosecond pulsed electric fields," Pigment Cell Melanoma Research, Apr. 2, 2010, 23, 554-563.

Chen, X. et al., "Comparative study of nanosecond electric fields in vitro and in vivo on hepatocellular carcinoma indicate macrophage infiltration contribute to tumor ablation in vivo," PLOS.One, vol. 1, No. 9, e86421, pp. 1-7 (Jan. 2014).

Chen, X. et al., "Long Term Survival of Mice With Hepatocellular Carcinoma after Pulse Power Ablation with Nanosecond Pulsed Electric Fields," Technol. Cancer Res. Treat. 11, 83-93 (2012).

Cole et al. 2001, Time-domain whole-field fluorescence lifetime imaging with optical sectioning; Journal of Microscopy, vol. 203, Pt. 3, Sep. 2001, pp. 246-257.

Cook et al., "Design and Testing of a Fast, 50 kV Solid-State Kicker Pulser," IEEE 2002, pp. 106-109.

Cossarizza et al. 2001. Chapter 21, Analysis of Mitochondria during Cell Death. In Methods in Cell Biology, vol. 63, pp. 467-486.

Craft et al. 1998, "PhLPs and PhLOPs in the phosducin family of G beta gamma binding proteins," American Chemical Society, Biochemistry 37: pp. 15758-15772.

Cubeddu et al. 2002, Time-resolved fluorescence imaging in biology and medicine; Topical Review; Institute of Physics Publishing, J. Phys.D; Appl.Phys, 35: pp. R61-R76.

DeAngelis L. M., 2001, Brain Tumors. New England Journal of Medicine, v. 344: pp. 114-123.

DeBruin et al., Modeling electroporation in a single cell. I. Effects offield strength and rest potential. Biophysical Journal, vol. 77, Sep. 1999, pp. 1213-1224.

Deng, J. et al., "The effects of intense submicrosecond electrical pulses on cells," Biophysical Journal, Apr. 2003, 84(4) 2709-2714. English Translation of JP2013223115A provided via Google Patents on Oct. 17, 2018, https://patents.google.com/patent/JP2013223115A/en?q=surgical&q=glasses&q=camera&oq=surgical+glasses+camera.

European Application No. 15865400.4, Extended European Search Report dated Jul. 17, 2018, 7 pages.

Frank et al., 1998. High-power Pseudospark and BLT switches. IEEE Trans. Plasma Science 16(2): pp. 317-323.

Freeman et al., 1994, Theory of electroporation of planar bilayer membranes: predictions of the aqueous area, change in capacitance, and pore-pore separation. Biophysical Journal, vol. 67, Jul. 1994: pp. 42-56.

Gabriel, B. et al, "Generation of reactive-oxygen species induced by electropermeabilization of Chinese hamster ovary cells and their consequence on cell viability." Eur. J. Biochem. 223, 25-33 (1994).

Garg, A.D. et al., "A novel pathway combining calreticulin exposure and ATP secretion in immunogenic cancer cell death," EMBO J. 31, 1062-1079 (2012).

Garg, A.D. et al., "Hypericin-based photodynamic therapy induces surface exposure of damage-associated molecular patterns like HSP70 and calreticulin," Cancer Immunol. Immunother. 61, 215-221 (2012).

(56) References Cited

OTHER PUBLICATIONS

Garon et al. "In Vitro and In Vivo Evaluation and a Case Report of Intense Nanosecond Pulsed Electric Field as a Local Therapy for Human Malignancies", Int. J. Cancer, vol. 121, 2007, pp. 675-682.
Garon et al., 2007, In Vitro and In Vivo Evaluation and a Case Report of Intense Nanosecond Pulsed Electric Field as a Local Therapy for Human Malignancies. Int. J. Cancer, vol. 121, pp. 675-682.
Gaudreau et al., "Solid-State Pulsed Power Systems for the Next Linear Collider," IEEE 2002, pp. 298-301.
Gilbert et al. 1997. Novel electrode designs for electrochemotherapy. Biochimica et Biophys. Acta vol. 1334, pp. 9-14.
Gotoh et al. 2002. Nitric Oxide-induced Apoptosis in RAW 264.7 Macrophages Is Mediated by Endoplasmic Reticulum Stress Pathway Involving ATF6 and CHOP. J. Biol. Chem. vol. 277, No. 14, Apr. 2002: pp. 12343-12350.
Grekhov et al. 1983. Formation of Nanosecond High-Voltage Drop Across Semiconductor Diodes with Voltage Recovery by a Drift Mechanism. Sov. Tech Phys. Lett., vol. 9, No. 4: pp. 188-189.
Grekhov et al. 2000 Physical Basis for High-Power Semiconductor Nanosecond Opening Switches. IEEE Transactions on Plasma Science, vol. 28: pp. 1540-1544.
Grekhov et al. 2005. Nanosecond Semiconductor Diodes for Pulsed Power Switching. Physics-Uspekhi, vol. 48, No. 7: pp. 703-712.
Gundersen et al. "Nanosecond Pulse Generator Using a Fast Recovery Diode", IEEE 26.sup.th Power Modulator Conference, 2004, pp. 603-606.
Hemker et al. 1999. Development of a parallel code for modeling plasma based accelerators. IEEE Particle Accelerator Conference 5: pp. 3672-3674.
Hennings et al. 1985. Induction of papillomas with a high probability of conversion to malignancy. Carcinogenesis vol. 6, pp. 1607-1610.
Hennings et al. 1986. Malignant conversion and metastasis of mouse skin tumors: a comparison of SENCAR and CD-1 mice. Environmental health perspectives, vol. 68, pp. 69-74.
Hewlett Packard. 1984. Application Note 918, Pulse and Waveform Generation with Step Recovery Diodes. Oct. 1984. 22 pages.
International Application No. PCT/US09/45073, International Search Report dated Dec. 18, 2009, 2 pages.
International Application No. PCT/US15/63025, International Search Report and Written Opinion dated Apr. 21, 2016, 9 pages.
International Application No. PCT/US2017/015881, Invitation to Pay Additional Fees and, Where Applicable, Protest Fee, mailed Mar. 15, 2017, 2 pages.
Jiang et al., "Marx Generator Using Power Mosfets," IEEE 2009, pp. 408-410.
Joshi et al. 2000. Electroporation dynamics in biological cells subjected to ultrafast electrical pulses: A numerical simulation study, Physical Review E, vol. 62, Jul. 2000: pp. 1025-1033.
Kirbie et al., "An All Solid State Pulse Power Source for High PRF Induction Acceslerators," IEEE 1998, pp. 6-11.
Kirkman et al. 1986. Low pressure, light initiated, glow discharge switch for high power applications. Appl. Phys. Lett., vol. 49, Sep. 1986: pp. 494-495.
Kotnik et al. 2000. Theoretical evaluation of the distributed power dissipation in biological cells exposed to electric fields, Bioelectromagnetics, vol. 21: pp. 385-394.
Kotov et al., A Novel Nanosecond Semiconductor Opening Switch for Megavolt Repetitive Pulsed Power Technology: Experiment and Applications. In Proceedings of the 9th Int. IEEE Pulsed Power Conference, Albuquerque, NM, 1993, pp. 134-139.
Krasnykh et al., "A Solid State Marx Type Modulator for Driving a TWT," Conference Record of the 24th International Power Modulator Symposium 2000, pp. 209-211.
Kroemer, G. et al., "Classification of cell death: recommendations of the Nomenclature Committee on Cell Death 2009," Cell Death Differ. Jan. 2009; 16(1): 3-11. Published online Oct. 10, 2008. doi: 10.1038/cdd.2008.150.
Krysko, D.V. et al., "Clearance of apoptotic and necrotic cells and its immunological consequences," Apoptosis, 11, 1709-1726 (2006).
Krysko, D.V. et al., "Immunogenic cell death and DAMPs in cancer therapy," Nature Reviews | Cancer, 12, 860-875 (Dec. 2012).
Kudo, M., "Hepatocellular carcinoma in 2011 and beyond: from the pathogenesis to molecular targeted therapy," Oncology. 81 Suppl 1:1-10. Epub@Dec. 22, 2011, 1-10 (2011).
Li et al. 2002. Retinoic acid upregulates cone arrestin expression in retinoblastoma cells through a Cis element in the distal promoter region. Invest Ophthalmol Vis Sci., vol. 43, No. 5, May 2002: pp. 1375-1383.
Li et al. 2003. Gene expression networks underlying retinoic acid-induced differentiation of human retinoblastoma Cells Invest Ophthalmology & Vision Science, vol. 44, No. 3, Mar. 2003: pp. 996-1007.
Long, G. et al., "Targeted tissue ablation with nanosecond pulses," IEEE Trans. Biomed. Eng. 58, 2161-2167 (2011).
Lucas, M.L. et al., "IL-12 Gene therapy using an electrically mediated nonviral approach reduces metastatic growth of melanoma," DNA and Cell Biology, 2003, 22(12) 755-763.
Lyubutin et al. 1997. Repetitive Nanosecond All-Solid-State Pulsers Based on SOS Diodes. In IEEE 11th International Pulsed Power Conference, Baltimore, MD: pp. 992-998.
Marcu et al. 1999. Photobleaching of arterial fluorescent compounds: characterization of elastin, collagen, and cholesterol time-resolved spectra during prolonged ultraviolet irradiation, Photochem. Photobiol., vol. 69, No. 6: pp. 713-721.
Marszalek et al. 1990. Schwan equation and transmembrane potential induced by alternating electric field, Biophysical Journal, vol. 58, Oct. 1990: pp. 1053-1058.
Maytin et al. 2001. Stress-Inducible Transcription Factor CHOP/gadd153 Induces Apoptosis in Mammalian Cells via p38 Kinase-Dependent and -Independent Mechanisms. Exp. Cell Res., vol. 267: pp. 193-204.
Moll et al. 1969. Physical Modeling of the Step Recovery Diode for Pulse and Harmonic Generation Circuits. In Proceedings of the IEEE, vol. 57, No. 7, Jul. 1969: pp. 1250-1259.
Nader Yatim et al., "RIPK1 and NF-κ3 signaling in dying cells determines cross-priming of CD8$^+$T cells," Science, Oct. 2015, vol. 350, Issue 6258, pp. 328-335, sciencemag.org.
Nuccitelli et al., "Nanoelectroablation of Murine Tumors Triggers a CO8-Dependent Inhibition of Secondary Tumor Growth," PLoS One, vol. 10, No. 7, Jul. 31, 2015, 17 pages.
Nuccitelli et al., "Nano-Pulse Stimulation is a physical modality that can trigger immunogenic tumor cell death," Journal for ImmunoTherapy of Cancer, Apr. 17, 2017, vol. 5, No. 32, 14 pages.
Nuccitelli, R. et al., "Nanoelectroablation of human pancreatic carcinoma in a murine xenograft model without recurrence," Int. J. Cancer 132, 1933-1939 (Apr. 15, 2013).
Nuccitelli, R. et al., "Nanoelectroablation therapy for murine basal cell carcinoma," Biochem. Biophys. Res. Commun. 424, 446-450 (2012).
Nuccitelli, R. et al., "Nanosecond pulsed electric field stimulation of reactive oxygen species in human pancreatic cancer cells is Ca2+-dependent," Biochem. Biophys. Res. Commun. 435, 580-585. (Jun. 14, 2013).
Nuccitelli, R. et al., "Nanosecond pulsed electric fields cause melanomas to self-destruct," Biochem. Biophys. Res. Commun. 343, 351-360 (2006).
Nuccitelli, R. et al., "Non-thermal nanoelectroablation of UV-induced murine melanomas stimulates an immune response," Pigment Cell Melanoma Res., 25:618-629 (2012).
Obeid, M. et al., "Calreticulin exposure dictates the immunogenicity of cancer cell death," Nat. Med. 13, 54-61 (Jan. 2007).
Okamura et al. "Development of the High Repetitive Impulse Voltage Generator Using Semiconductor Switches," IEEE 1999, pp. 807-810.
Pakhomova, O.N. et al., "Oxidative effects of nanosecond pulsed electric field exposure in cells and cell-free media," Arch. Biochem. Biophys. 527, 55-64 (2012).
PCT/US2017//032744, "International Search Report" dated Jul. 21, 2017, 2 pages.

(56) References Cited

OTHER PUBLICATIONS

PCT/US2017/015881, International Search Report dated May 25, 2017, 3 pages.
PCT/US2017/015884, "International Search Report," dated Apr. 21, 2017, 3 pages.
PCT/US2017/052340, "International Search Report", dated Jan. 8, 2018, 2 pages.
Pogue et al. 2001. In Vivo NADH Fluorescence Monitoring as an Assay for Cellular Damage in Photodynamic Therapy; Photochemistry and Photobiology, vol. 74, No. 6, Oct. 2001: pp. 817-824.
Polevaya et al. 1999. Time domain dielectric spectroscopy study of human cells. II. Normal and malignant white blood cells. Biochim. Biophys. Acta., vol. 1419: pp. 257-271.
Redondo et al., "Solid-State Marx Generator Design with an Energy Recovery Reset Circuit for Output Transformer Association," Power Electronics Specialists Conference, IEEE, 2007, 5 pages.
Ren et al., "An apoptosis targeted stimulus with nanosecond pulsed electric fields (nsPEFs) in E4 squamous cell carcinoma," Apoptosis, 2011, vol. 16, pp. 382-393.
Richter-Sand et al., "Marx-Stacked IGBT Modulators for High Voltage, High Power Applications," IEEE 2002, pp. 390-393.
Rukin, S.N. 1999. High-Power Nanosecond Pulse Generators Based on Semiconductor Opening Switches (Review). Instruments and Experimental Techniques, vol. 42, No. 4: pp. 439-467.
Sack et al., "Design Considerations for a Fast Stacked-MOSFET Switch," IEEE Transactions on Plasma Science, vol. 41, No. 10, Oct. 2013, pp. 2630-2636.
Sanders et al. 2008. Broadband Power Measurement of High-Voltage, Nanosecond Electric Pulses for Biomedical Applications. IEEE International Power Modulator Conference, Las Vegas, NV, 2008, pp. 350-353.
Schoenbach et al. 1997. The Effect of Pulsed Electric Fields on Biological Cells: Experiments and Applications, IEEE Transactions on Plasma Science, vol. 25, Apr. 1997: pp. 284-292.
Schoenbach, K.H., "Bioelectric effect of intense nanosecond pulses in Advanced Electroporation Techniques in Biology and Medicine," Eds. Pakhomov, A.G., Miklavcic, D. & Markov,M.S., 19-50, Taylor and Francis Group, Boca Raton (2010).
Slaga, T. J. 1986. SENCAR mouse skin tumorigenesis model versus other strains and stocks of mice. Environmental health perspectives, vol. 68, pp. 27-32.
Sylvester et al., "Effects of ultra-wideband electromagnetic pulses on pre-neoplastic mammary epithelial cell proliferation," Cell Prolif., 2005, vol. 38, pp. 153-163.
Tang et al. 2007. Diode Opening Switch Based Nanosecond High Voltage Pulse Generators for Biological and Medical Applications. IEEE Transactions on Dielectrics and Electrical Insulation, vol. 14, No. 4, pp. 878-883.
Vernier, P.T. et al., "Calcium bursts induced by nanosecond electric pulses," Biochem. Biophys. Res. Commun. 310, 286-295 (2003).
Wakita et al. 1995. Some Characteristics of the Fluorescence Lifetime of Reduced Pyridine Nucleotides in Isolated Mitochondria, Isolated Hepatocytes, and Perfused Rat Liver In Situ. J. Biochem., vol. 118: pp. 1151-1160.
Wang et al. 2005. Solid-State High Voltage Nanosecond Pulse Generator. IEEE Pulsed Power Conference, pp. 1199-1202.
Watanabe et al. 2002. Feasibility and limitations of the rat glioma model by C6 gliomas implanted—at the subcutaneous region. Neural. Res., vol. 24, No. 5, Jul. 2002: pp. 485-490.
Weaver et al. 1996. Theory of Electroporation: A Review. Bioelectrochemistry and Bioenergetics, vol. 41: pp. 135-160.
Webb et al. 2002. A wide-field time-domain fluorescence lifetime imaging microscope with optical sectioning. Review of Scientific Instruments, vol. 73, No. 4, Apr. 2002: pp. 1898-1907.
Weiss et al. 1984. The Role of T3 surface molecules in the activation of human T cells: a two-stimulus requirement for IL 2 production reflects events occurring at a pre-translational level. The Journal Immunology, vol. 133, No. 1, Jul. 1984: pp. 123-128.
White, J.A. et al., "Stimulation of capacitative calcium entry in HL-60 cells by nanosecond pulsed electric fields," J. Biol. Chem. 279, 22964-22972 (2004).
Wu et al., "Nanosecond pulsed electric fields as a novel drug free therapy for breast cancer: An in vivo study," Cancer Letters, Oct. 4, 2103, vol. 343, No. 2, pp. 268-274.
Yao et al., "FPGA-Controlled All-Solid-State Nanosecond Pulse Generator for Biological Applications," IEEE Transactions on Plasma Science, vol. 40, No. 10, Oct. 2012, pp. 2366-2372.
Yin et al., "Cutaneous Papilloma and Squamous Cell Carcinoma Therapy Utilizing Nanosecond Pulsed Electric Fields (nsPEF)", 2012, PLoS One vol. 7, No. 8, pp. e43891-e43891.
Yin et al., "Nanosecond pulsed electric field (nsPEF) treatment for hepatocellular carcinoma: A novel locoregional ablation decreasing lung metastasis," Cancer Letters, 346:285-291 (2014).
Zhu et al. 2000. The carboxyl terminal domain of phosducin functions as a transcriptional activator. Biochemical and Biophysical Research Communications, vol. 270, pp. 504-509.

\* cited by examiner

NANOELECTROABLATION CONTROL AND VACCINATION

CROSS-REFERENCES TO RELATED APPLICATIONS

The present application is a continuation of U.S. non-provisional application Ser. No. 16/040,434 filed Jul. 19, 2018, which is a continuation of U.S. non-provisional application Ser. No. 15/671,014 filed Aug. 7, 2017 (now U.S. Pat. No. 10,058,383 issued Aug. 28, 2018), which is a division of U.S. Non-provisional application Ser. No. 14/954,630, filed Nov. 30, 2015 (now U.S. Pat. No. 9,724,155 issued Aug. 8, 2017), which claims priority to U.S. Provisional Patent Application No. 62/086,025, filed Dec. 1, 2014, which applications are incorporated herein by references in this entirety.

STATEMENT AS TO RIGHTS TO INVENTIONS MADE UNDER FEDERALLY SPONSORED RESEARCH AND DEVELOPMENT

This invention was made with government support under award numbers R01CA125722 and R44CA150484 awarded by the National Institutes of Health (NIH). The government has certain rights in the invention.

BACKGROUND

Hepatocellular carcinoma (HCC) is the third leading cause of cancer-related death worldwide and the ninth leading cause in the US. According to the International agency for Research on Cancer, HCC is the fifth most common cancer in men (523,000 cases per year with 7.9% of all cancer cases) and the seventh most common cancer in women (226,000 cases per year with 6.5% of all cancer cases). For patients with lesions less than 2 cm, radiofrequency ablation (RFA) under ultrasound guidance is the recommended treatment.

RFA works by heating the tissue to hyperthermic levels for several minutes resulting in necrosis. Two weaknesses of this technique are the lack of a sharp boundary to the ablation zone and poor ablation around vessels and ducts. Since the spread of heat depends on the thermal conductivity of the tissue, it is difficult to control the precise boundary of this ablation zone. In addition, the presence of heat sinks such as large vessels or ducts allows heat to be carried away from the tissue near the vessel and makes it difficult to reach the temperature required to ablate tissues in those regions.

BRIEF SUMMARY

Rather than causing thermal damage to the tumor, nanosecond pulsed electric field (nsPEF) therapy uses ultrashort, high voltage electric pulses that generate transient nanopores in cell and organelle membranes leading to the initiation of programmed cell death in the tumor cells while depositing very little energy into the tissue. This can be called "nanoelectroablation." When applied to a rat orthotopic hepatocellular carcinoma model, the treated tumor is ablated and leads to the production of cytotoxic T-cells that attack an implanted secondary tumor that is implanted 3 weeks later. Since the ablation zone is determined by a specific electric field threshold, it exhibits a very sharp boundary that is not influenced by fluid flow in vessels or ducts. The mechanism of cell death induced by the treatment described in the disclosure is indicative of immunogenic cell death (ICD).

Immunogenic cell death has been characterized over the past 10 years as a cell death modality by which a series of damage-associated molecular patterns (DAMPs) are exhibited. The appearance of DAMPs may be essential for the stimulation of an immune response and general anticancer immunity in vivo. Traditionally, this cell death modality has been initiated by certain chemotherapeutic drugs such as anthracyclines, oxaliplatin, and mitoxantrone. A possible requirement for ICD is the combined action of reactive oxygen species (ROS) and endoplasmic reticulum (ER) stress. The ER stress mediated by Ca' release may lead to another important component of the signaling pathway in ICD, the translocation of calreticulin (CRT) from the ER to the cell surface to become an additional "eat me" signal for programmed cell death. Surface CRT binds to CD91 and CD69 on dendritic cells to promote phagocytosis, facilitating their tumor antigen presentation and incitement of tumor antigen-specific cytotoxic T-cells.

Nanoelectroablation of orthotopic HCC tumors leads to immunogenic cell death as characterized by caspase activation and CRT exposure. Nanoelectroablation of HCC tumors can lead to the production of antitumor immunity, mediated by $CD8^+$ T-cells.

Similarly, nanoelectroablation of fibrosarcoma tumors can lead to the production of antitumor immunity conditioned by $CD8^+$ T-cells.

DETAILED DESCRIPTION

Precise ablation with a nanopulsed (sub-microsecond) multi-electrode can be realized by visualization of an imaginary contour line of a threshold value of an electric field surrounding the electrodes. A threshold value of about 12 kV/cm has been shown to produce a very sharp boundary between ablated and nonablated tissue.

Visualization of the 'critical' boundary can assist a surgeon, researcher, or other operator. The visualization can be performed by a synthetic overlay onto a video image of the electrode on a display screen. The display screen can be affixed to glasses worn by the operator (e.g., GOOGLE GLASS® wearable display), or it can be a separate screen. Alternatively, a projection device can project an image of contour lines onto a tumor that is to be ablated.

An instrument tracking system can detect a location and orientation of the instrument's electrodes. The instrument tracking system may be camera-based or use other sensors for detecting the electrodes.

For fine control, an electrode apparatus can be anchored to a tumor of a subject, and an outline of the tumor against healthier tissue can be captured. Using the outline, as well as a modeled location of an imaginary contour line of an electric field, the electrode apparatus can be positioned and moved so that the contour line is parallel to, adjacent, or otherwise aligns with the interface between the tumor and the healthier tissue.

Ablation Zone

Figure 1:
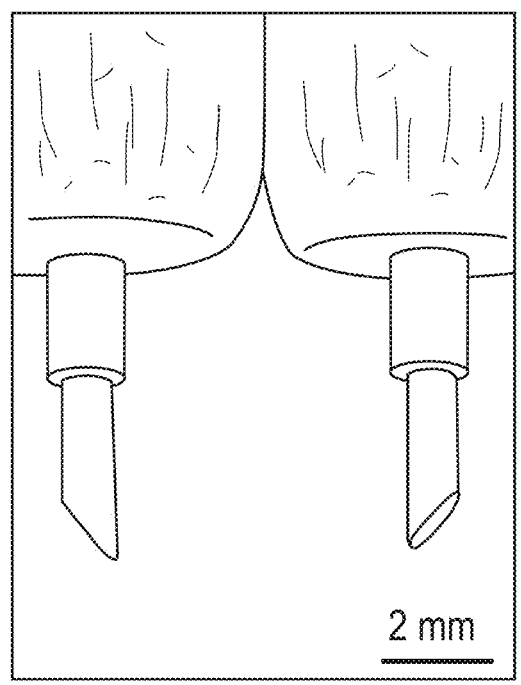
FIG. 1 is a picture of a two-needle electrode in accordance with an embodiment.

FIG. 1 shows a two-needle electrode for an experiment where the inventors first treated several rat livers with the two-needle electrode in order to identify the electrode's ablation zone, i.e. the tissue region exhibiting apoptosis.

Figure 2:
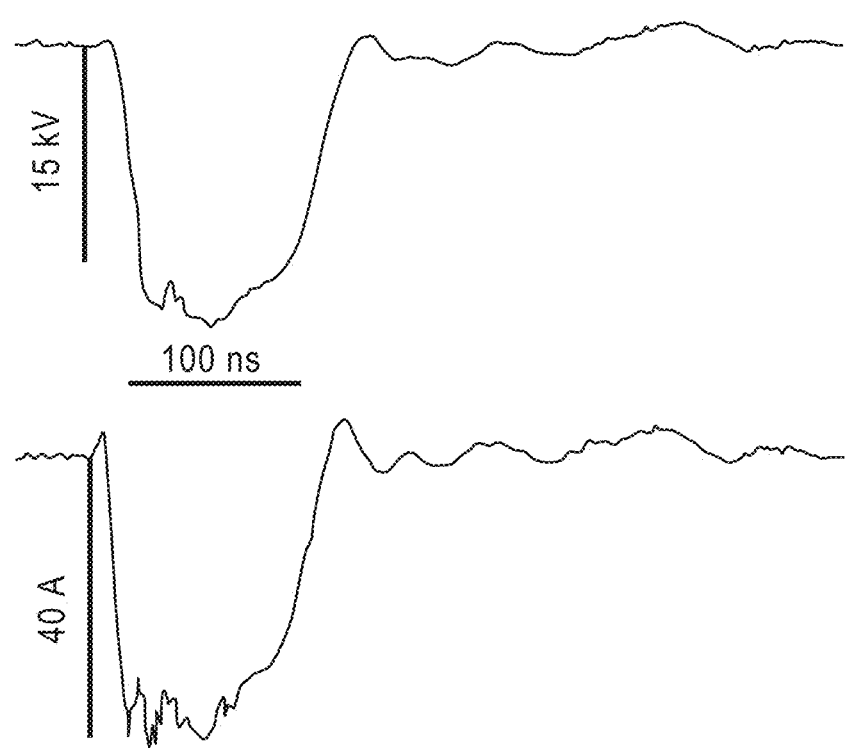
FIG. 2 shows voltage and current waveforms delivered by the electrode of FIG. 1 to a rat liver.

FIG. 2 shows a pulse from the experiment.

An early indicator of apoptosis is the shrinkage of nuclei known as pyknosis which occurs within 2 hours after treatment. In order to map the pyknosis region, thin sections were generated from the treated tissue that was fixed 2 hours after treatment. They were stained with hematoxylin and eosin (H&E) stain. When these thin sections were illuminated from the side, the apoptotic region scattered light more effectively than the non-apoptotic region, probably due to the high concentration of red blood cells in the region.

Figure 3:
FIG. 3 is a scattered light image of a treated liver in accordance with an embodiment.

FIG. 3 shows an image of such a section. It was confirmed that the reflective region coincided with the pyknotic region.

Figure 4:
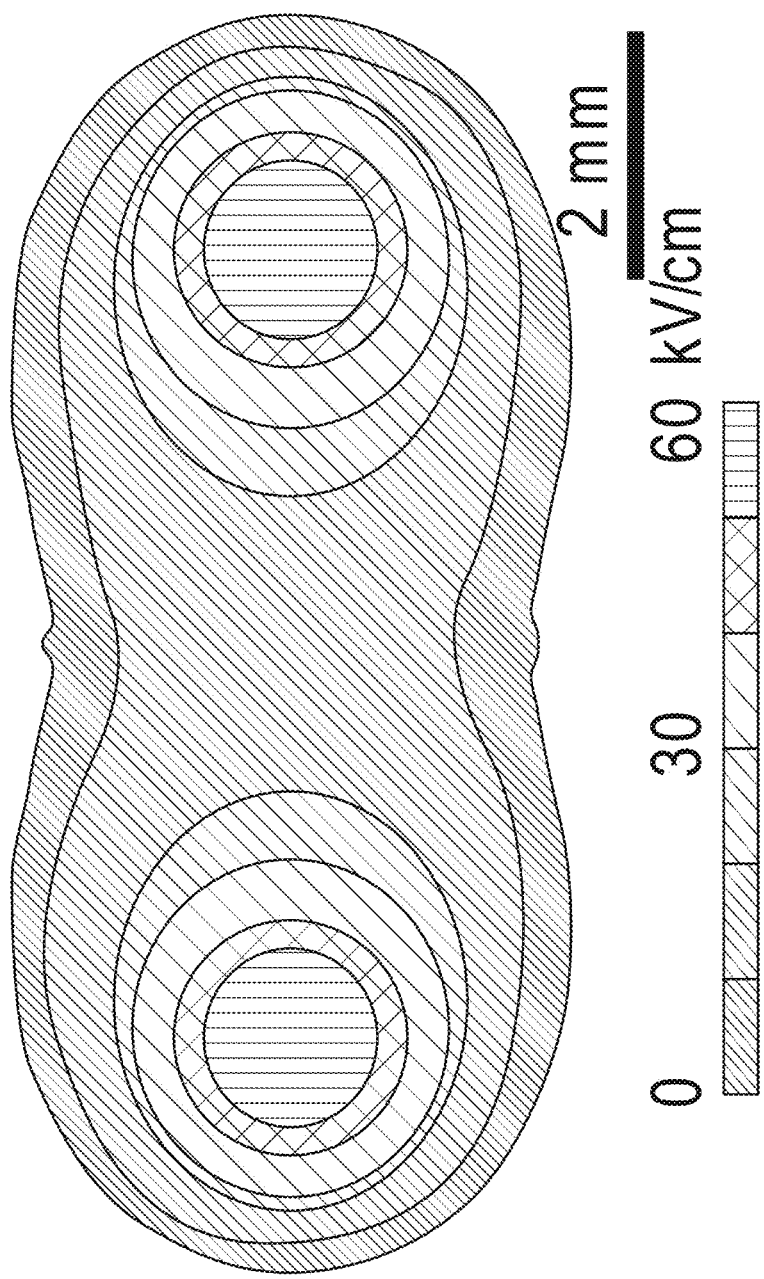
FIG. 4 illustrates a model of a predicted electric field generated by the electrode of FIG. 1A. The outer boundary represents a 12 kV/cm field line.

FIG. 4 shows a model of an electric field. In particular, the electric field distribution around the electrodes was modeled, and it was found that the 12 kV/cm boundary coincides quite well with the ablation zone boundary.

nsPEF Treatment

A three mm-long two-needle electrode was used to nanoelectroablate the liver tumors (FIG. 1). The liver lobe to be impaled was supported from below by the plastic handle of a scalpel while the electrode was inserted into the liver to surround the tumor. Exactly 400 pulses, 100 ns long, and 15 kV in amplitude delivering 50 A with a 20 ns rise time were applied. A preliminary study ablating normal liver tissue confirmed that the application of 400 pulses with this electrode was sufficient to completely ablate a dumbbell-shaped liver region 0.5 by 1 cm in size.

Pulse Generator

All treatments were applied using a 100 ns pulse generator (Electroblate, Inc.) that charges a pulse-forming network of capacitors and inductors and delivers 15 kV to the electrodes each time a pressure-controlled spark gap fires. Pulses were applied at 4 pps and the pulse waveform is shown in FIG. 2. The typical pulse rise time was less than 20 ns, and a typical pulse delivered 50 A of current or 0.08 J into the liver tissue.

Electric Field Modeling

The two-electrode field modeling results were generated using a 3D model of the geometry. By applying rules of symmetry, only one quadrant of the model was meshed. Sharp joints in the model are avoided to reduce computational instabilities, and a sufficiently fine tetrahedral mesh is used to properly capture field enhancements due to curvatures. Meshing is done with Gmsh: a three-dimensional finite element mesh generator (www.geuz.org/gmsh). Field modeling is performed assuming electro-static conditions. Insulators are considered perfect in that they have infinite resistivity. The tissue between the needles is considered homogeneous. Since only electric field strength is of interest, resistivity of the tissue is of little-to-no importance. Computation was done with a general environment for the treatment of discrete problems (www.geuz.org/getdp). The underlying equations are those for electrostatics and have been validated with known analytical solutions. The voltage difference between the electrodes is 15 kV and is assumed to come from an ideal source without impedance (shown in FIG. 4).

Confirming Apoptosis Initiation by Cleaved Caspase 3 and 9

One of the hallmarks of apoptosis is the activation of caspases 3 and 9 by cleavage. Immunohistochemistry was conducted on thin sections of tissue taken from both control, untreated tumors sampled two weeks after injection into the liver and nanoelectroablated tumors collected 2 hours after treatment.

Untreated controls showed very low levels of cleaved caspase 3 and 9 while tumor tissue collected 2 hours after treatment showed relatively high levels of cleaved caspase 3 and 9 as expected.

Calreticulin Translocation to the Cell Surface Following nsPEF Treatment

Figure 5:
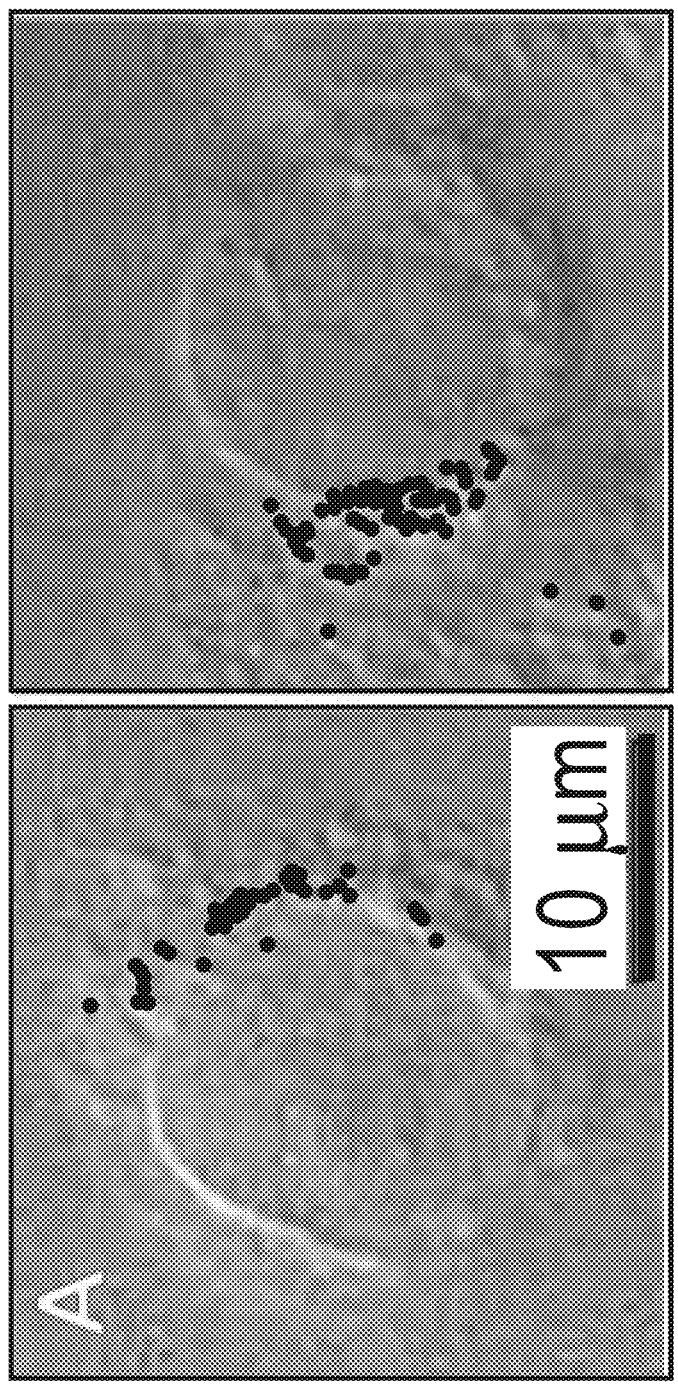
FIG. 5 shows calreticulin labeling on the surface of two typical McA-RH7777 liver tumor cells that had been exposed to nsPEF.
Figure 6:
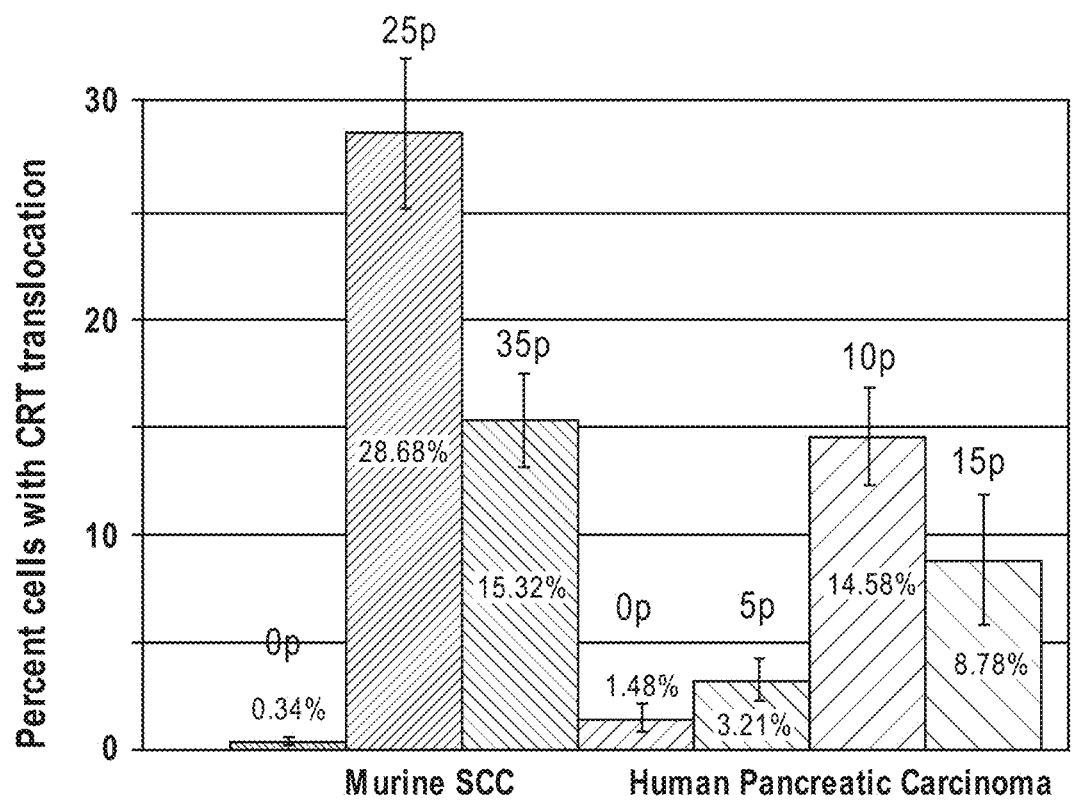
FIG. 6 shows the percentage of nsPEF-treated cells exhibiting surface calreticulin v. the number of pulses applied at 15 kV/cm.

One of the potentially critical initiation steps in immunogenic apoptosis is the translocation of calreticulin from the ER to the plasma membrane. Labeling cells with an antibody to calreticulin has shown that calreticulin translocation can be detected about 2 hours after nsPEF treatment as shown in FIG. 5. The number of cells with surface calreticulin exhibits a dependence on the number of pulses applied as shown in FIG. 6.

Nanoelectroablation of the First Tumor Results in Growth Inhibition of the Second Tumor Secondary tumors injected 3 weeks after nanoelectroablation of the primary tumor were looked at one week after injection, and their growth rate was compared with that of the primary tumor that had been ablated in the same rat.

The liver was surgically exposed, and tumor cells were injected beneath the capsule of one liver lobe in 6 rats. After suturing closed the incision, 1 week went by before reopening and treating the tumor with 400 pulses (100 ns, 15 kV) applied between needles 6 mm apart center-to-center (as shown in FIG. 1). The incision was sutured, and three weeks went by for an immune response to develop. The liver was surgically exposed again to allow the injection of tumor cells beneath the capsule of another liver lobe. The incision was closed, and one week went by for the second tumor to grow. The animal was sacrificed, and the entire liver was removed for photographs and histological analysis. These second tumors failed to grow well and, in two instances, could not be found at all. The mean area of those tumors that were found exhibited only 3% of the mean area exhibited by the first tumors after the same 1 week of growth.

Depletion of $CD8^+$ T-Cells Reverses the Growth Inhibition of the Second Tumor

Figure 7:
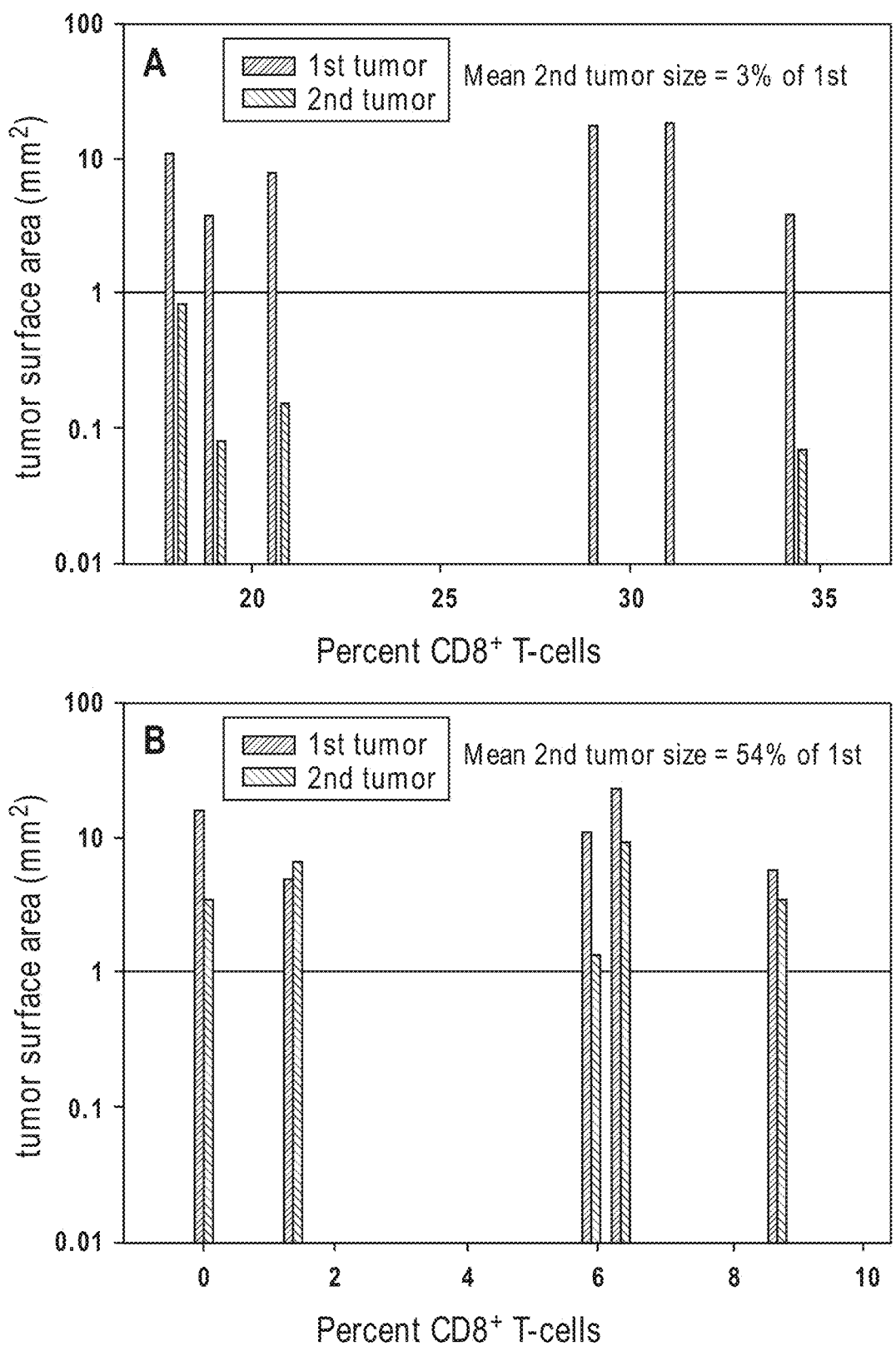
FIG. 7 shows graphs comparing first and second tumor surface areas.

FIG. 7 shows graphs comparing 1st and 2nd tumor surface areas using plot A and plot B. As shown in plot A, the secondary tumor size is much smaller than the primary tumor after the same 1 week of growth when $CD8^+$ levels are high. Plot B shows that the secondary tumor is more similar to the primary tumor size when $CD8^+$ levels are reduced. One characteristic of the adaptive immune response is the generation of $CD8^+$ cytotoxic T-cells that specifically kill cells with surface antigens to which they are targeted. A test for the involvement of $CD8^+$ T-cells in an apparent immune response is to use specific antibodies to these cells to deplete them from the animal and determine if this has any effect on the apparent immune response.

Next, primary tumors were again nanoelectroablated with the same nsPEF treatment in another group of 5 rats. But 1 day prior to the second injection of tumor cells an intraperitoneal (IP) injection of 250 μg of the anti-rat $CD8^+$ monoclonal antibody, OX-8, was performed. Blood samples were collected before and at least 24 hours after injection to confirm the depletion of $CD8^+$ cells. One week went by after injecting the second tumor before sacrificing the rat and processing the liver for immunohistochemistry. As shown in FIG. 7, the second tumors grew much faster under $CD8^+$-depleted conditions with the mean 2nd tumor size 54% of the 1st tumor and in one case it was larger than the first tumor.

Immunohistochemistry detects $CD8^+$ T-cells within the tumor.

In order to directly investigate the presence of $CD8^+$ T-cells within the nanoelectroablated tumors, fixed tumors were sectioned and incubated with an antibody to this surface molecule. Untreated control tumors showed sparse labeling of CD8. Sections of tumors removed 7 days after nanoelectroablation exhibited much greater labeling. The enhanced presence of the $CD8^+$ cytotoxic T-cells suggests that they are involved in inhibiting tumor growth.

Murine Fibrosarcoma Tumor Cells

In a demonstration of vaccination embodiments of the invention, murine fibrosarcoma tumor cells (MCA205) were treated with a sufficient number of 100 ns pulses to induce apoptosis and then injected subdermally into syngeneic mice. After waiting 3 weeks for an immune response to develop, 'healthy' (untreated) MCA205 cells were injected subdermally to form a tumor. Under all control conditions, each tumor grew very well, growing to 8 times its initial size in 2 weeks. This includes tumors in mice that had been vaccinated with saline as well as those vaccinated with cells treated with mitomycin C to kill them by necrosis. However, when fresh tumor cells were injected subdermally into mice that had been vaccinated with nsPEF-treated MCA205 cells, the tumors did not grow. Instead, they actually shrank. This suggests the involvement of an immune response.

To confirm, the adaptive immune system was implicated, $CD8^+$ cytotoxic T-cells were depleted with an antibody to CD8 one day prior to injecting the fresh tumor cells in some mice. In those mice, the cells grew a tumor at a rate that is very similar to that of the controls.

Figure 8:
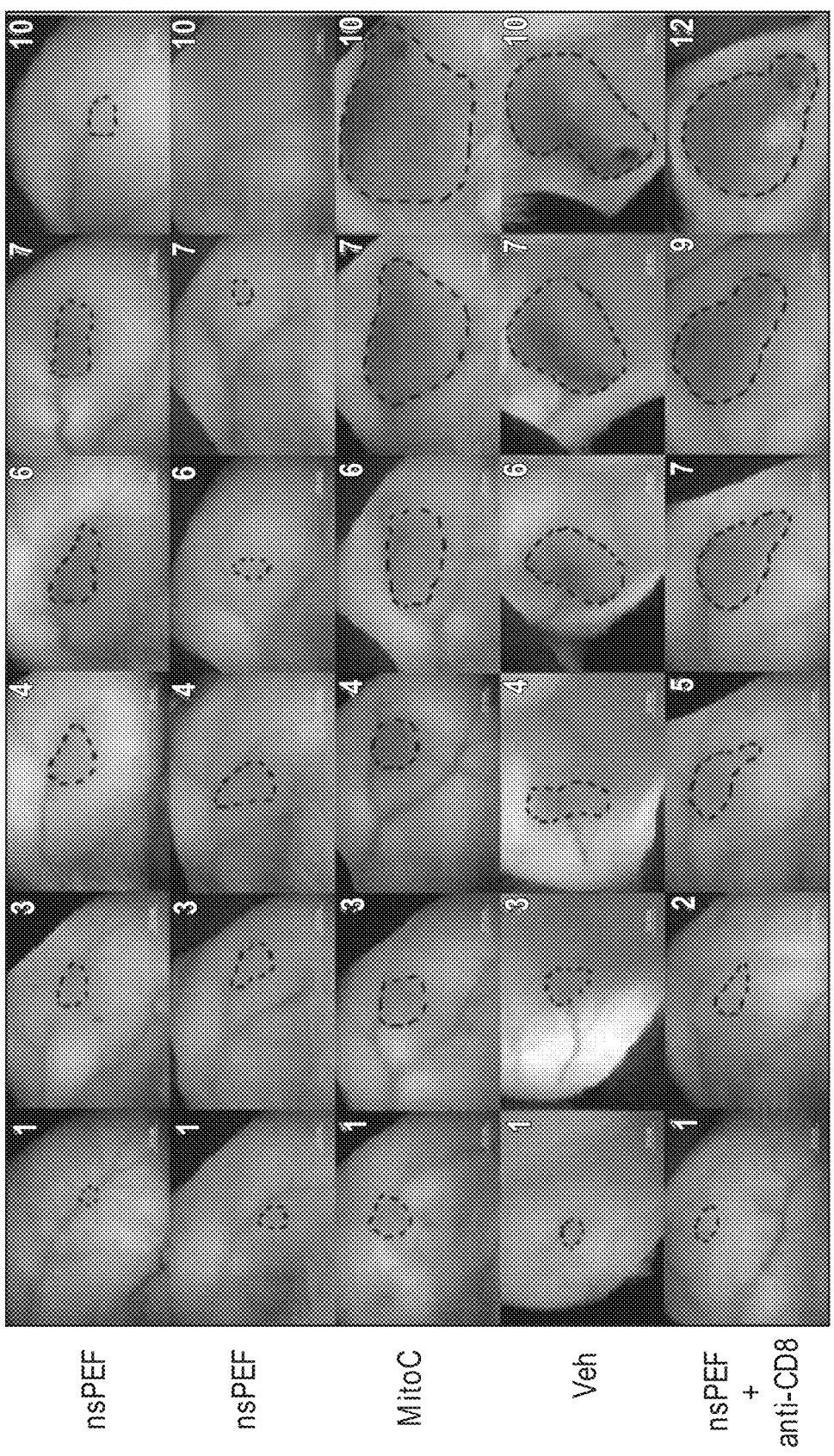
FIG. 8 contains images of transilluminated murine skin under which MCA205 cells have been injected. Dotted lines outline the tumor in each image.

FIG. 8 contains images of transilluminated murine skin under which MCA205 cells have been injected. The mice were first vaccinated with either treated tumor cells or vehicle and 3 weeks later healthy tumor cells were injected to form the tumors outlined. "NsPEF" indicates that the mice were vaccinated with nsPEF-treated tumor cells. "MitoC" indicates that the mice were vaccinated with mitomycin C-treated tumor cells that causes necrosis. "nsPEF+anti-CD8" indicates that the mice were vaccinated with nsPEF-treated tumor cells and anti-CD8 antibodies were injected IP 1 day before the healthy tumor cells were injected. One million ($10^6$) MCA205 cells were injected on day 0. The subsequent tumor formed by these injected cells is outlined with a dotted line in each photo taken on the day after injection indicated in the upper right of each image. The top two rows show two separate mice that were vaccinated with nsPEF-treated MCA205 cells 3 weeks earlier. The secondary tumors grew slightly but then disappeared. The third, "MitoC" row shows the growth of a tumor that resulted from MCA205 cells injected into a mouse that had been vaccinated with necrotic cells resulting from mitomycin C exposure. The tumor grew. The fourth, "Veh" row shows the growth of a tumor that resulted from the injection of MCA205 cells into a mouse vaccinated with saline vehicle. Again, the tumor grew. The fifth, "nsPEF+anti-CD8" row shows the growth of a tumor that resulted from the injection of MCA205 cells into a mouse vaccinated with nsPEF-treated cells one day after the intraperitoneal injection of 100 μg of anti-CD8 antibody. The tumor grew, indicating $CD8^+$ cells were involved in attacking the secondary tumors in the first two rows.

Figure 9:
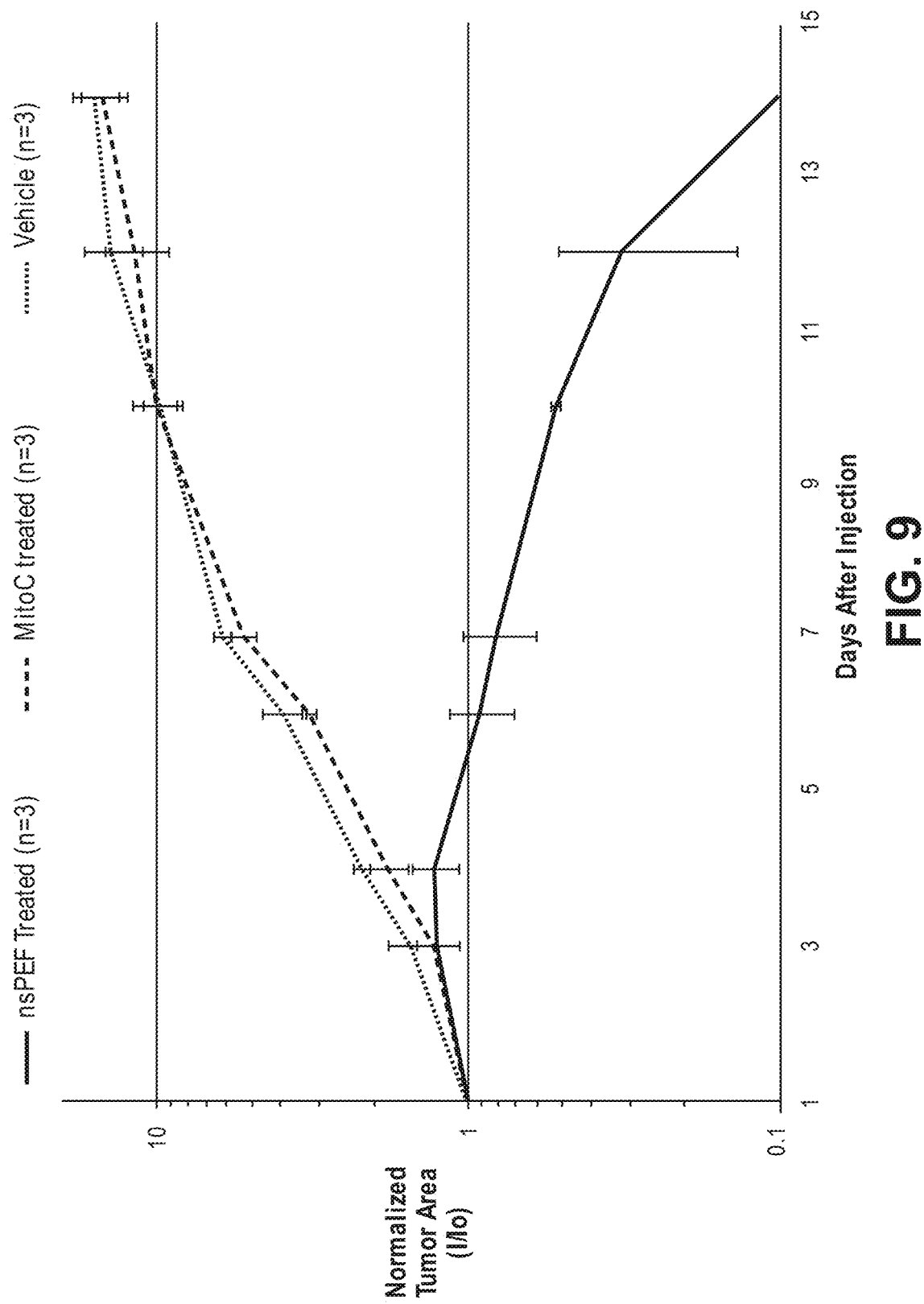
FIG. 9 is chart of mean normalized tumor areas from three mice with respect to days after injection of MCA205 tumor cells.

FIG. 9 is a chart of mean normalized tumor areas from three vaccinated mice with respect to days after injection of MCA205 tumor cells. Shown in the figure is a mean normalized tumor area in mice vaccinated 3 weeks before by injecting either nsPEF-treated tumor cells, necrotic tumor cells that were killed by mitomycin C exposure, or saline vehicle. MitoC refers to vaccination with necrotic cells that had been treated with mytomycin C. Prior vaccination with nsPEF-treated tumor cells resulted in the inhibition of tumor growth, as indicated by the fall of the solid line. This is in contrast to the two control vaccinations, which apparently had no inhibitory effect on the tumor growth. Error bars represent SEM with N=3.

Figure 10:
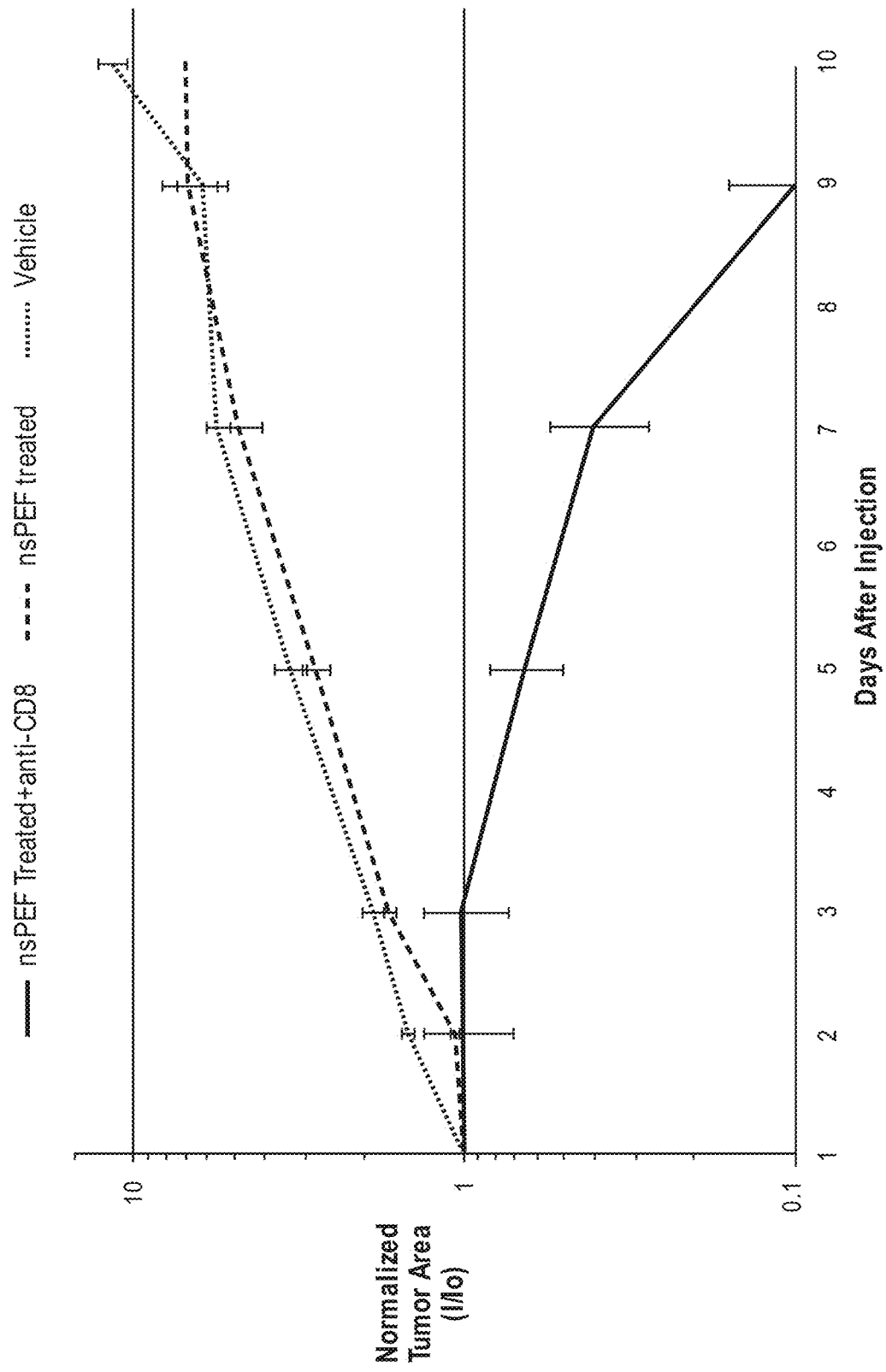
FIG. 10 is chart of mean normalized tumor areas from six mice with respect to days after injection of MCA205 tumor cells.

FIG. 10 is a chart of mean normalized tumor areas from six vaccinated mice with respect to days after injection of MCA205 tumor cells. Mice were first vaccinated with either nsPEF-treated tumor cells or vehicle and in one group anti-CD8 antibody was injected 1 day before injecting the healthy tumor cells. To normalize, each tumor area is divided by the original area on day 1 so that the graph starts at "1," and "2" would represent a doubling of the initial tumor area. Shown in the figure is a mean normalized tumor area in mice vaccinated 3 weeks before injecting tumor cells with either nsPEF-treated tumor cells, saline vehicle, or nsPEF-treated cells 24 hours after intraperitoneal injection of anti-CD8 antibody. The tumors grew very quickly in mice vaccinated with control saline and nsPEF-treated cells when CD8 antibody had depleted the CD8+ T-cells. However, vaccination with nsPEF-treated tumor cells resulted in complete inhibition of tumor growth, as shown by the falling solid line. Error bars represent SEM with N=6.

DISCUSSION

Stimulation of the adaptive immune system following tumor nanoelectroablation has been demonstrated. Cytotoxic CD8+ T-cells are enriched in secondary tumors injected 3 weeks after the primary tumor was nanoelectroablated and depleting these CD8+ cells allows the secondary tumor to grow much more rapidly. It is likely that nsPEF treatment acts to trigger immunogenic apoptosis because the transient nanopore generation elicits both reactive oxygen species (ROS) and endoplasmic reticulum (ER) stress. The large electric field imposed on the cell by the nsPEF drives water into the lipid membranes to form nanopores that allow Ca' to flow into the cytoplasm from both outside the cell and from ER stores. The loss of Ca' stresses the ER, and the increase in cytoplasmic Ca' triggers ROS generation. Therefore, it appears that the physical process of generating transient nanopores in cellular membranes results in the same ROS formation and ER stress observed previously with certain chemotherapeutic drugs to be required for calreticulin translocation to the plasma membrane to initiate the immune response.

Nanoelectroablation offers a non-thermal, precisely targeted mechanism to trigger immunogenic cell death in tumors. The murine melanoma allograft work demonstrated that nanoelectroablation was superior to surgical excision at accelerating secondary tumor rejection in immune-competent mice but not in immunodeficient mice. This suggested enhanced stimulation of a protective immune response by nsPEF treatment, and that was further supported by the presence of CD4+ T-cells within the treated tumors as well as within untreated tumors in mice with other melanomas that had been treated with nanoelectroablation at least 19 days earlier.

Here, a direct test for the nsPEF-induced stimulation of the adaptive immune response results in a greatly enhanced secondary tumor growth by specifically depleting CD8+ cytotoxic T-cells. This enhanced secondary tumor growth suggests that these cytotoxic T cells are indeed inhibiting tumor growth. This conclusion is further supported by immunohistochemistry data showing that these CD8+ T-cells are concentrated within shrinking tumors.

The implications of this are profound as it raises the possibility that nanoelectroablating one tumor could enlist the immune system to attack untreated metastases or even unablated regions of the original tumor if it is slow growing. This immunogenic characteristic of nanoelectroablation may be the most important characteristic of this ablation modality. This naturally raises the possibility that nsPEF-treated tumor cells might be used to vaccinate animals against the tumor. This possibility was directly tested by vaccinating mice with nsPEF-treated tumor cells 3 weeks prior to injecting healthy tumor cells subdermally. The results from 6 mice are striking. Every one of them failed to grow a tumor from this secondary injections (FIG. 10), suggesting a very strong growth inhibition is occurring. The reversal of this growth inhibition following the depletion of cytotoxic T-cells supports our hypothesis that these CD8+ T-cells are involved in the inhibition of tumor growth.

Immunogenic Cell Death in Other Ablation Modalities

Electrochemotherapy with bleomycin may also induce hallmarks of immunogenic cell death. Eight pulses 100 µs long, 1.3 kV/cm may be sufficient to stimulate calreticulin externalization and ATP release, but the presence of bleomycin was required for HMGB1 release. Moreover, "vaccination" with ECT-treated cancer cells protects mice against subsequent challenge with normal cancer cells. Additional ablation modalities eliciting immunogenic cell death include radiation therapy, photodynamic therapy, and microwave thermal ablation. These latter two may provide protection against subsequent challenge by vaccination. It is not clear what these diverse modalities have in common that allows them all to stimulate immunogenic cell death. One common characteristic of electrochemotherapy, radiation therapy, and photodynamic therapy (but not yet for microwave thermal ablation) is ROS stimulation. Therefore, ROS may be the common link between these modalities. A point is that enlisting the immune system to attack metastases adds a very powerful advantage to these ablation techniques over other ablation methods that do not trigger ICD.

In some embodiments, tumor cells from a diseased animal tissue culture may be treated with nsPEF and then used for vaccination in other animals. NsPEF treatment of the tumor may occur in vivo, ex vivo, or in vitro. Sub-microsecond pulsed electric fields, such as those at 15 kV, 400 repetitions at 100 ns each (at up to seven Hz) can be effective against the tumor cells such that they express calreticulin. The calreticulin-expressing tumor cells can then be introduced by injection, or otherwise, into an otherwise healthy animal. The injected calreticulin-expressing tumor cells can trigger an immune response in the second animal, better preparing it for battle against like cancer tumors. The second animal's immune response can be closely observed in order to track the progress of antibody production and final elimination of the tumor cells.

In some embodiments, only those tumor cells that have calreticulin expressed over a substantial portion (e.g., 1%, 2%, 3%, 4%, 5%, 7%, 10%, 15%, 20%, 25%, and up) of their cell membranes may be sorted from lesser or non-calreticulin-expressing cells. The higher-expressing cells can then be injected into the healthy animal.

Tumor Cell Injection

In an experiment, one million McA-RH7777 cells in 15 µl of HBSS were added to 15 µl MATRIGEL® cell substrate (available from Corning Inc., New York, U.S.A.) that had been allowed to thaw on ice. The solution was mixed to create a homogenous suspension and kept on ice until the time of injection. A sterile insulin syringe in sealed packaging was also kept on ice until the time of injection. In order to expose the liver for injection, an abdominal incision 3-4 cm long was made on the midline posterior to the xiphoid while the rat was under isoflurane inhalation anesthesia. The 30 µl solution containing $10^6$ cells was injected under the capsule of one liver lobe. A two-layer closure was completed using absorbable sutures for the peritoneum/muscle layer and wound clips for the skin. One week later the liver was exposed again and photographed, and the tumor was treated with the 2-needle electrode delivering 400 pulses at 15 kV amplitude delivering 50 A for 100 ns duration (see FIGS. 1 and 2). After waiting 3 weeks to allow sufficient time for an immune response to be mounted, the liver was exposed again and a second injection of tumor cells was made into another lobe of the liver. One week later the liver was exposed again and photographed to document the size of the second tumor and the rat was euthanized. In some experiments 250 µl of anti-CD8 antibody (Cat #:

MCA48EL, BioRad-AbD Serotec) was injected IP 1 day before the second injection of tumor cells to deplete $CD8^+$ T-cells.

Measuring $CD8^+$ T-Cell Levels

500 µl blood was drawn from tail vein using heparinized capillary tubes. Blood samples were treated with ACK until all erythrocytes were lysed, spun down, and exposed to 5% PFA. Samples were then washed and pellet resuspended and deposited on charged slides. Samples were then stained using CD3 (Bio-Rad, cat # MCA772GA) and CD4 (BioLegend, San Diego, Calif.) antibodies, and mounted using DAPI-containing Anti-Fade Mounting Medium. Slides were then imaged using fluorescence microscopy, and images were analyzed by manually counting total number of cells displaying both DAPI and CD3 staining and subtracting the amount of CD4 stained cells from the total. Both OX-8 IP injected animals and non-injected animals were used, as well as untreated animals.

Immunohistochemistry

Liver tissue was fixed in 10% buffered formalin for several days before embedding in paraffin and preparing 5 µm sections. Cleaved caspase 3 and 9 were probed for as well as $CD8^+$ T-cells in sections from treated tumors that had been prepared using standard procedures of deparaffinization and antibody labeling. Cleaved caspase 3 and 9 rabbit anti-rat antibodies were obtained from Cell Signaling Technology (cat. #9664P, 9507S). Anti-CD8 antibody was obtained from AbD Serotec (cat. # MCA48EL). Fluorescently labeled secondary goat anti-rabbit antibodies were then used to label the primary antibodies. The calreticulin antibody was obtained from GeneTex (cat. # GTX62353).

Visualization

Figure 11:
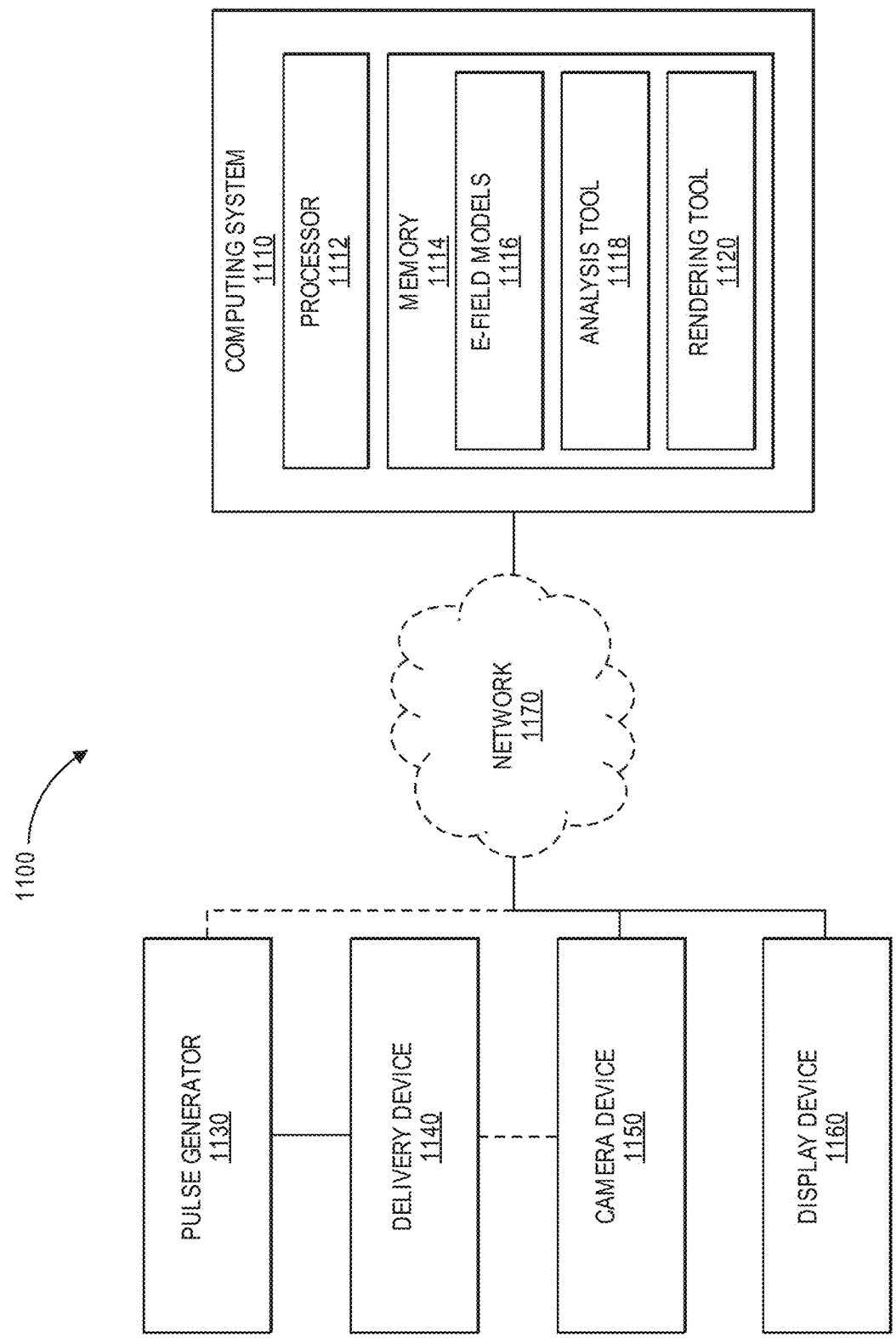
FIG. 11 illustrates an overall visualization system in accordance with an embodiment.

FIG. 11 illustrates an overall example visualization system 1100 in accordance with an embodiment. An operator, such as a surgeon, operates the system 1100 or portions of the system 1100 to perform an operation on a subject, such as a human patient. The system 1100 enables the operator to visualize aspects of the operation. In an example, the operation includes applying an electric field to treat a tumorous area. The visualization includes an imaginary contour line of a threshold value of the electric field. In a further example, the visualization also includes feedback related to positioning the imaginary contour line with respect to the tumorous area.

As illustrated in FIG. 11, the system 1100 includes a computing system 1110, a pulse generator 1130, a delivery device 1140, a camera device 1150, and a display device 1160. Some of these components may be integrated. For example, the camera device 1150 can be integrated with the delivery device 1140 as further illustrated in FIG. 13. In addition, the system 1100 can include a network 1170 for interconnecting some or all of these components. For example, the network 1170 represents a data network that communicatively couples the computing system 1110 with the camera device 1150, the display device 1160, and optionally the pulse generator 1130. Some of the components can also be interconnected independently of the network 1170. For example, the delivery device 1140 can be directly connected to the pulse generator 1130. In this example, the delivery device 1140 is operated locally or via the pulse generator 1130 rather than remotely via the computing system 1110 over the network 1170. Each of these components is described in more detail herein next.

Turning to the computing system 1110, it includes a processor 1112 and a memory 1114. Depending on the configuration of the computing system 1110, the memory 1114 can be volatile (such as random access memory (RAM)) and/or non-volatile (such as read-only memory (ROM), flash memory, etc.) and can include removable storage and/or non-removable storage such as, but not limited to, magnetic storage, optical disks, tape storage, and/or other non-transitory computer-readable media. The memory 1114 stores computer-readable instructions, data structures, program modules, and other data for the computing system 1110. For example, the memory 1114 includes an operating system and various applications. An application represents a set of instructions that, when executed by the processor 1112, provide various functionalities. Examples of such applications include electric field models 1116, an analysis tool 1118, and a rendering tool 1120.

The electric field models 1116 are models for different electric fields. Each electric field model can be derived through modeling, simulation, and/or experiments. In an example, an electric field model includes an imaginary contour line of a threshold value of an electric field. The imaginary contour line, or equivalently the electric field model, is defined for a configuration of the delivery device 1140 (e.g., a configuration of the electrodes of the delivery device 1140), the type of cancer, and/or settings of the electric field. As illustrated in FIGS. 2-4, the electric field distribution around two electrodes was modeled, and it was found that the 12 kV/cm boundary coincides quite well with the ablation zone boundary. As such, the electric field model corresponding to the electrode configuration, cancer, and electric field settings of FIGS. 2-4 includes an imaginary contour line around the 12 kV/cm boundary (e.g., a line around dumbbell-shaped liver region 0.5 by 1 cm in size).

In addition, an electric field changes (e.g., deformed) depending on the environment where the electric field is applied. For example, using the same electric settings, the electric field changes when applied in free space, to a skin tissue of a subject (e.g., a human), and to a muscle tissue of the subject. The environment's permittivity is one factor that impacts the change. Another factor is the environment's geometry.

In an embodiment, an electric field model also accounts for the environment (e.g., free air, skin tissue, muscle tissue, etc.). The different impacting factors (permittivity, geometry, etc.) of the various environments can be set as parameters for the modeling, simulation, and/or experiments to generate the electric field model. As such, the imaginary contour line, or equivalently the electric field model, is defined for also the environment and/or the different factors.

The analysis tool 1118 is configured to analyze various data related to operating the pulse generator 1130, delivery device 1140, and/or camera device 1150, and, accordingly, provide instructions to the operator. The analysis applies a proper electric field model of the electric field models 1116 to derive the instructions. For example, the computing system 1110 has access to electric data of the pulse generator 1130, position data and electrode configuration data of the delivery device 1140, image data of the camera device 1150, and cancer related data. Based on the electric data, electrode configuration data, and cancer data, the analysis tool 1118 selects the proper electric field model. Based on the position data and image data, the analysis tool 1118 generates an overlay of the imaginary contour line over images provided by camera device 1150. In an example, these images show a portion of the delivery device (e.g., the electrodes) and tumorous area. As such, the overlay shows the imaginary contour line positioned relatively to the portion of the delivery device and tumorous area. In addition, the analysis tool 1118 generates feedback for properly positioning the portion of the delivery device (e.g., the electrodes) over the tumorous area.

The rendering tool 1120 is configured to present an output of the analysis tool 1118 at the display device 1160. For example, the rendering tool 1120 enables the visualization of the overlay and, optionally, the feedback at the display device 1160.

The pulse generator 1130 is configured to supply high voltage pulses. In an example, the pulse generator 1130 includes a 100 ns pulse generator (available from Electroblate, Inc.) that charges a pulse-forming network of capacitors and inductors and delivers 15 kV each time a pressure-controlled spark gap fires. The electric pulses are delivered to the subject via the delivery device 1140.

The delivery device 1140 is configured to deliver electric energy to the subject. In an example, the delivery device 1140 includes a surgical electrode tool having a set of electrodes. The set of electrodes generates electric fields from the electric pulses. Different sets of electrodes, each of which representing an electrode configuration, are available and can be interchangeably attached to the delivery device 1140. For instance, one set of two electrodes can be attached to the delivery device 1140 and then removed and replaced with another set of three electrodes (or other electrode configurations) in a plug-and-play manner.

Data about the electrode configuration of the delivery device 1140 is used as an input to the analysis tool 1118 for selecting an electric field model. This data is accessible to the computing system 1110 based on a variety of techniques. In one example technique, the operator enters the data at a user interface of the computing system 1110. For instance, the operator enters the number of electrodes or a code specific to the electrode configuration at a keyboard, mouse, or touch screen display of the computing system 1110. In another example technique, the computing system 1110 detects the data automatically. For example, the delivery device 1140 can include a plug-and-play interface for attaching a set of electrodes. In turn, the interface includes a pinout, where different pins are activated based on the set of electrodes. Activation can involve shorting to ground, energizing to a particular voltage, disconnecting (i.e., making a high impedance connection), or otherwise as known in the art. Data about the activated pins are transmitted to the computing system 1110. The analysis tool 1118 compares this data to a table of pinouts to detect the electrode configuration.

In addition to the electrodes, the delivery device 1140 optionally includes a tracking system. The tracking system is configured to track positions and/or orientations of the delivery device 1140. In an example, the tracking system can use global positioning system (GPS)-based or local positioning determination systems to determine precise positions, and orientation can be determined by accelerometers, fiducial tracking, or other means for determining an angle orientation in space.

The camera device 1150 is configured to provide image data, such as video, to the computing system 1110. In an example, the camera device 1150 includes low light color camera of a proper form factor. For instance, the camera device 1150 can be integrated with the delivery device 1140. In this illustration, the camera device 1150 includes a CMOS camera sensor capable of imaging in the ultraviolet (UV) wavelength region (e.g., in an fluorescent light environment) and/or infrared region. The camera device 1150 also includes a circuit board with firmware for generating the associated video. The CMOS camera sensor can be installed at a pinhole of the plug-and-play interface of the delivery device 1140 such that the CMOS camera sensor is centered between (or at some other relative location) the attached electrodes. The circuit board can be installed in the body of the delivery device 1140. In a further illustration, the delivery device 1140 may also include a light source at the plug-and-play interface for illumination, thereby enhancing the imaging quality of the camera device 1150.

The display device 1160 is configured to display a visualization of some of the operations performed by the operator on the subject. In an example, the display device 1160 includes a fixed display, a heads-up display, a projection display, and/or a near eye display. The display device 1160 displays video received from the computing system 1110. The video includes an overlay of the imaginary contour line over images provided by camera device 1150 and, optionally, feedback for positioning the delivery device 1140.

The network 1170 is configured to communicatively couple the different components of the visualization system 1100. For example, the network 1170 can include a public or private data network such as the Internet or an Intranet, respectively. The network 1170 can also include a direct communication bus(es) between the components of the visualization system 1100.

Figure 12:
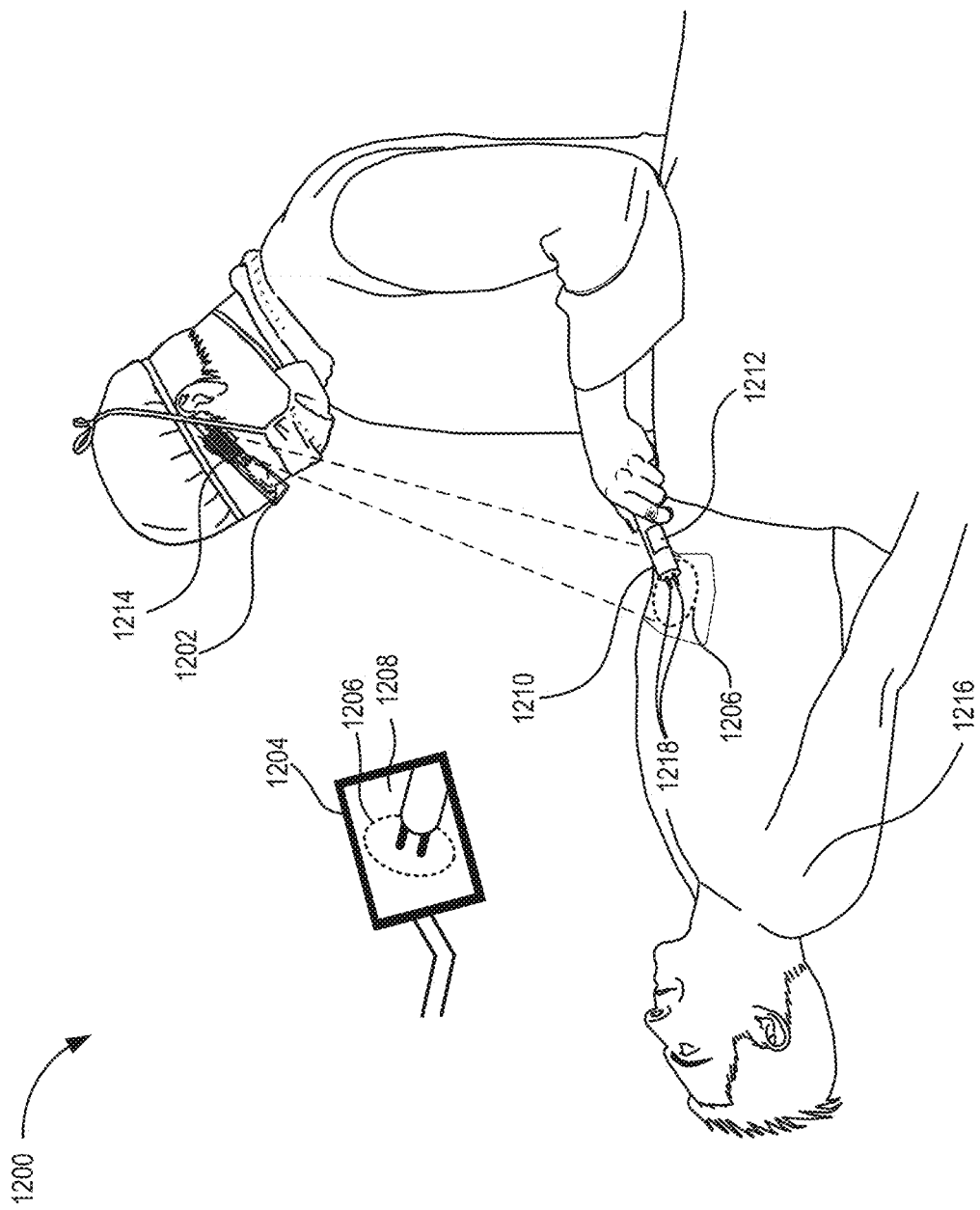
FIG. 12 illustrates an example visualization system in accordance with an embodiment.
Figure 13:
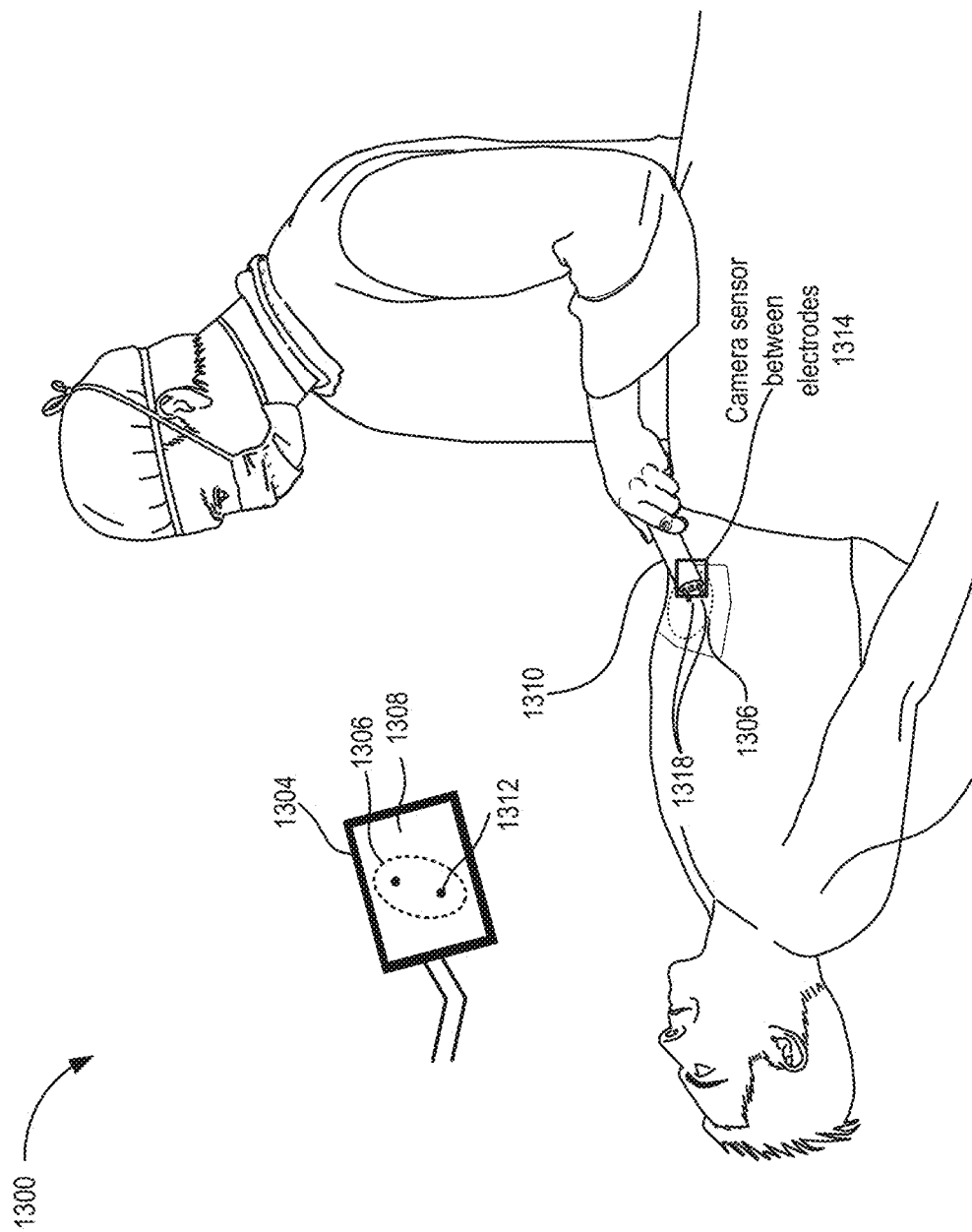
FIG. 13 illustrates another example visualization system in accordance with an embodiment.

Some or all of the components of the system 1100 may be integrated. In one example, the camera device 1150 is integrated with a display device 1160, as illustrated in FIG. 12. In another example, the camera device 1150 is integrated with the delivery device 1140 as illustrated in FIG. 13.

In yet another example, a computerized axial tomography (CT) scanner is used with the rendering tool. In this example, the CT scanner scans a subject (e.g., a human patient) in order to capture images of a tumor of the subject. Parts of the delivery device 1140 (e.g., electrodes) are placed into or onto the tumor, and the subject may be placed back into the CT scanner for another scan. From a CT scan image of the tumor, surrounding tissue, and radiopaque electrodes, a virtual boundary is drawn around the electrodes and displayed as an overlay of the CT image for an operator. The scans are processed by using image processing techniques of the computing system 1110 to detect the boundary of the tumor and the location of the electrodes and to overlay an imaginary contour line of a threshold value of the respective electric field over the boundary of the tumor. As such, the CT scans enable visualization of the imaginary contour line, such that an operator can subsequently adjust the insertion of the electrodes.

Hence, the visualization system 1100 of FIG. 11 represents a computing environment for enhancing certain operations of the operator. In particular, the visualization assists the operator when operating on the subject. For example, the operator can advantageously visualize the ablation zone relative to the tumorous area.

FIG. 12 illustrates an example visualization system 1200 in accordance with an embodiment. Components of the visualization system 1200 represent examples of some of the components of the visualization system 1100 of FIG. 11. In the visualization system 1200, human patient 1216 is operated on by a surgeon donning enhanced visualization glasses 1202 having a built-in display. A video camera 1214 is affixed to the glasses to image from the point of view of the wearer.

Images 1208 from the video camera 1214 can be displayed on a fixed display 1204. In the display of glasses 1202, or on the fixed display 1204, the view of a surgical electrode tool 1210 is augmented with a rasterized view of an imaginary contour line 1206. The imaginary contour line 1206 surrounds electrodes 1218 of the surgical electrode tool 1210 at a modeled threshold value of a peak, nominal, or root-mean-squared (RMS) electric field. For a rat liver, the threshold value is 12 kV/cm, which is where the electric field exhibits a sharp cutoff in nanoablation effectiveness.

The augmentation can be assisted by an onboard instrument tracking system 1212, which tracks an orientation and position of the surgical electrode tool 1210, specifically the electrodes 1218, with respect to the video camera's 1214 view angle. Tracking system can use global positioning system (GPS)-based or local positioning determination systems to determine precise positions, and orientation can be determined by accelerometers, fiducial tracking, or other means for determining an angle orientation in space.

FIG. 13 illustrates another example visualization system where a camera device and a delivery device are integrated, in contrast to FIG. 12, which illustrates the two devices as being separate. In the visualization system 1300 of FIG. 13, human patient 1316 is operated on by a surgeon. Sensors 1314 of a video camera are affixed to a pinhole of a surgical electrode tool 1310. Remaining hardware of the video camera (e.g., circuit board) are installed within the body of the surgical electrode tool 1310.

Images 1308 from the video camera can be displayed on a fixed display 1304. The images 1308 include a view of the ends 1312 (or some other actual or projected portions) of electrodes 1318 of a surgical electrode tool 1310. This view shows the electrodes 1318 as imaged by the video camera. In addition, the view is augmented with a rasterized view of an imaginary contour line 1306 on the fixed display 1304. The imaginary contour line 1306 surrounds the ends 1312 (or the other shown portions) of the electrodes 1318 at a modeled threshold value of a peak, nominal, or root-mean-squared (RMS) electric field. For a rat liver, the threshold value is 12 kV/cm, which is where the electric field exhibits a sharp cutoff in nanoablation effectiveness.

Figure 14:
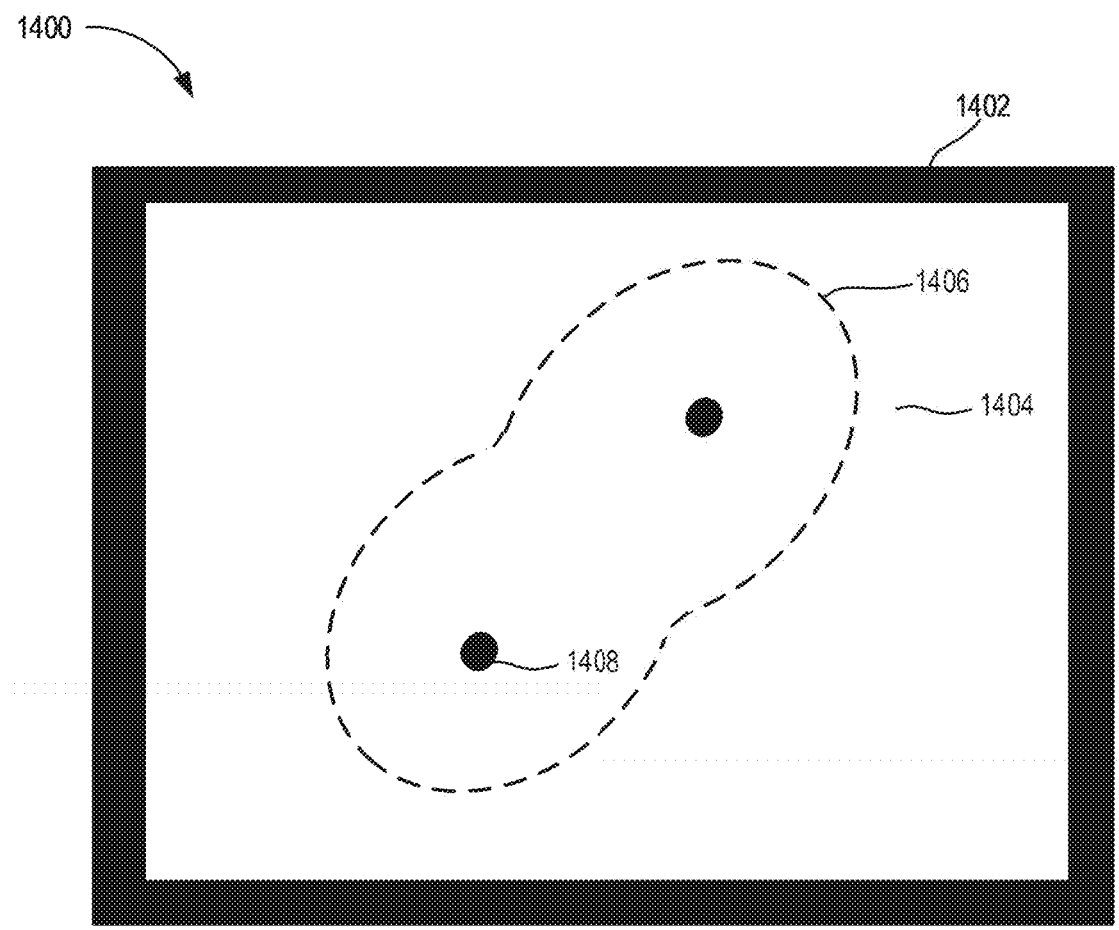
FIG. 14 illustrates a visualization in accordance with an embodiment.

FIG. 14 illustrates an example visualization 1400 available via the visualization system 1300 of FIG. 13. A similar visualization is also available for the visualization system 1200 of FIG. 12. As illustrated, the visualization 1400 is presented at a fixed display 1402 and includes an overlay of images 1404 of a video camera with an imaginary contour line 1406. A surgeon operates on a human patient to deliver energy from an electric field to a tumorous area via a surgical electrode device.

The images 1404 are captured by the camera device and show the operation area (not illustrated in FIG. 14). This operation area includes the tumorous area. The size of the shown operation depends on the field of view of the camera device. In addition, the images 1404 show the ends 1408 (actual or projected) of electrodes of the surgical electrode tool. Two ends 1408 are illustrated, reflecting an example use of a two electrode configuration.

The imaginary contour line 1406 traces a threshold value of the electric field, where the threshold value corresponds to the boundary of the ablation zone. This boundary depends the electric field, the electrode configuration, and/or type of cancer. Referring back to FIGS. 1-4 that use a two electrode configuration, a 12 kV/cm boundary coincides quite well with the ablation zone boundary for a liver cancer. The imaginary contour line traces the 12 kV/cm boundary and is illustrated in FIG. 14 as a line around dumbbell-shaped liver region 0.5 by 1 cm in size.

In an example, because the electric field changes with (e.g., also depends on) the environment where it is applied, the imaginary contour line 1406 is adjusted to account for the environment and/or the impacting factors of the environment (e.g., permittivity, geometry, etc.). For instance, when treating a skin tissue, a measurement of the patient's skin may be made for permittivity so that it can be modeled as a dielectric. In another illustration, the visualization of the field boundary can also be adjusted based on geometry of the treatment. For example, the boundary may be adjusted based on whether a tumor is being treated on a surface of the patient's skin versus whether the tumor is being treated inside the patient's body.

Figure 15:
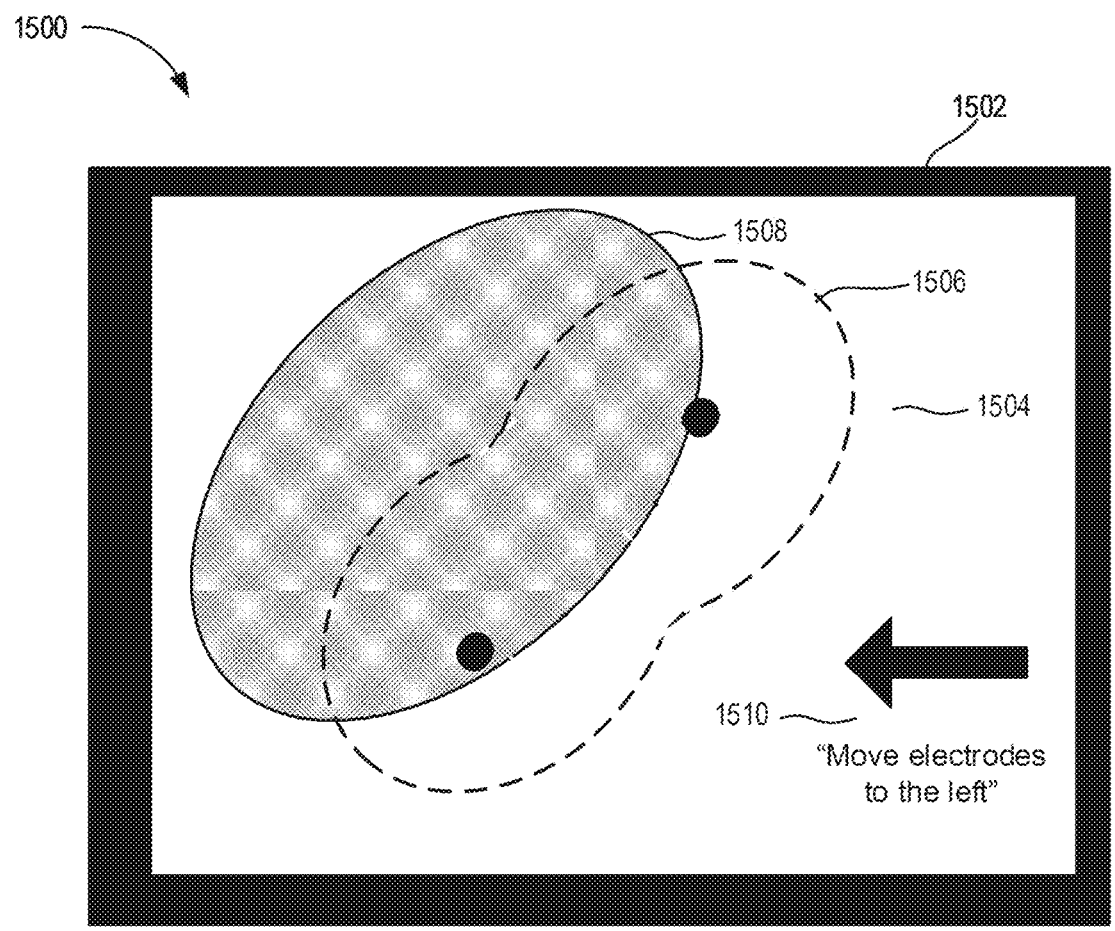
FIG. 15 illustrates a visualization with feedback in accordance with an embodiment.

FIG. 15 illustrates an example of a visualization that includes feedback for positioning a delivery device over a tumorous area. In particular, a visualization 1500 is presented at a fixed display 1502 and includes an overlay of images 1504 of a video camera, an imaginary contour line 1506, and a boundary 1508 of the tumorous area. A surgeon operates on a human patient to deliver energy from an electric field to the tumorous area via a surgical electrode device.

Similar to the images in the previous figure, the images 1504 are captured by the camera device and show the operation area and ends of electrodes. The imaginary contour line 1506 traces a threshold value of the electric field.

Prior to the operation, cancerous cells forming the tumorous area are fluorescently labeled. The video camera is capable of capturing the fluorescent light and generating the boundary 1508. For example, image processing and edge detection algorithms are applied to analyze and process images of the video camera and detect the boundary 1508. A line that traces the boundary 1508 is added to the overlay accordingly.

An analysis tool compares the relative positions of the imaginary contour line 1506 and the boundary 1508 of the tumorous area to generate the feedback 1510. The feedback 1510 provides instructions to correct misalignment detected based on the comparison. As illustrated in FIG. 15, the feedback 1510 instructs the operator to move electrodes of the surgical electrode device in a certain direction to properly position the imaginary contour line 1506 over the boundary 1508.

Figure 16:
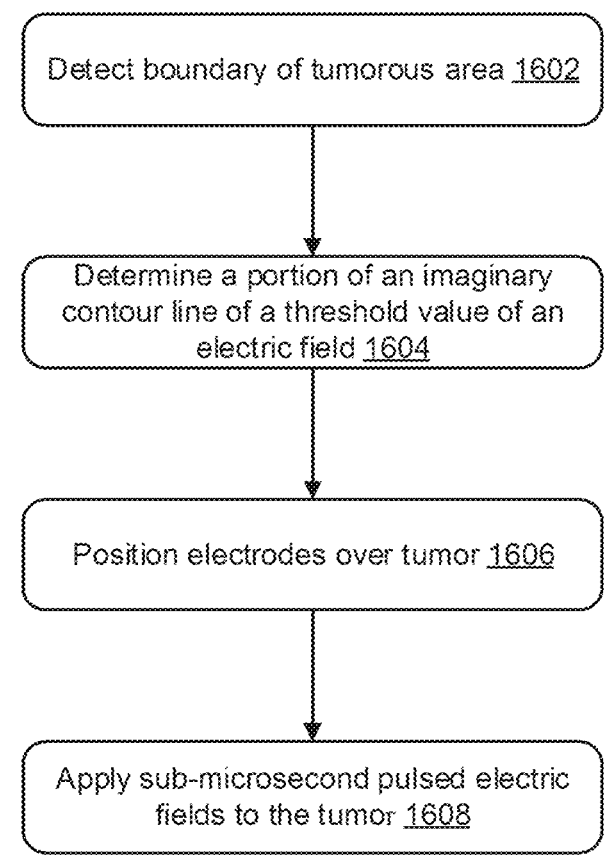
FIG. 16 illustrates a method of precisely treating a tumor with sub-microsecond pulsed electric fields in accordance with an embodiment.

Turning to FIG. 16, the figure illustrates an example method of precisely treating a tumor with sub-microsecond pulsed electric fields. The method could be performed by an operator on a subject, such as by a surgeon on a human patient. A visualization system, similar to the ones described in FIGS. 11-13, assists the operator in performing some or all operations of the method.

The example method starts at operation 1602, where a boundary of a tumorous area is detected. The boundary represents an interface between a tumor and non-tumor tissue in the subject. In an example, the operator has access to images of the subject's tissue. The images show the boundary based on a previous fluorescent labeling of the tissue. As such, the operator detects the boundary from the images. In an example, detecting the boundary includes using a CT scanner to image the tumor.

At operation 1604, a portion of an imaginary contour line of a threshold value of an electric field is determined. In an example, the visualization system assists the operator in determining this imaginary contour line. For instance, data about the tumor, an electrode configuration to be used, and settings of a pulse generated are accessible to the visualization system. Accordingly, an electric field model is selected. This model includes the imaginary contour line. The imaginary contour line is overlaid over images of the subject's tissue. The overlay is displayed to the operator, thereby enabling the operator to determine the portion of the imaginary contour line of the threshold value of the electric field.

In an example, the images are generated by the CT scanner such that determining the imaginary contour line includes using the CT scanner to image the electrode configuration. In yet another example, the images are generated by a camera device separate from the CT scanner.

At operation 1606, electrodes are positioned over the tumor. The electrodes are a part of a delivery device to generate the electric field. In an example, the operator positions the electrodes such that the imaginary contour line of the electric field aligns with the detected interface between the tumor and non-tumor tissue. In a further example, the visualization system assists the operator with this positioning. In particular, the visualization system also overlays feedback relative to the imaginary contour line and boundary positions. The feedback is presented at the display and instructs the operator to move the electrodes in a certain direction to correct any misalignment.

At operation 1608, sub-microsecond pulsed electric fields are applied to the tumor. In an example, once the electrodes are positioned, the operator operates the delivery device to deliver the electric fields. The electric fields are generated in high voltage pulses supplied by a pulse generator connected to the delivery device.

The visualization system assists the operator to perform some of the operations of the example treatment method of FIG. 16. This assistance includes presenting a visualization of the imaginary contour line and, optionally, feedback to position the electrodes over the tumor.

Figure 17:
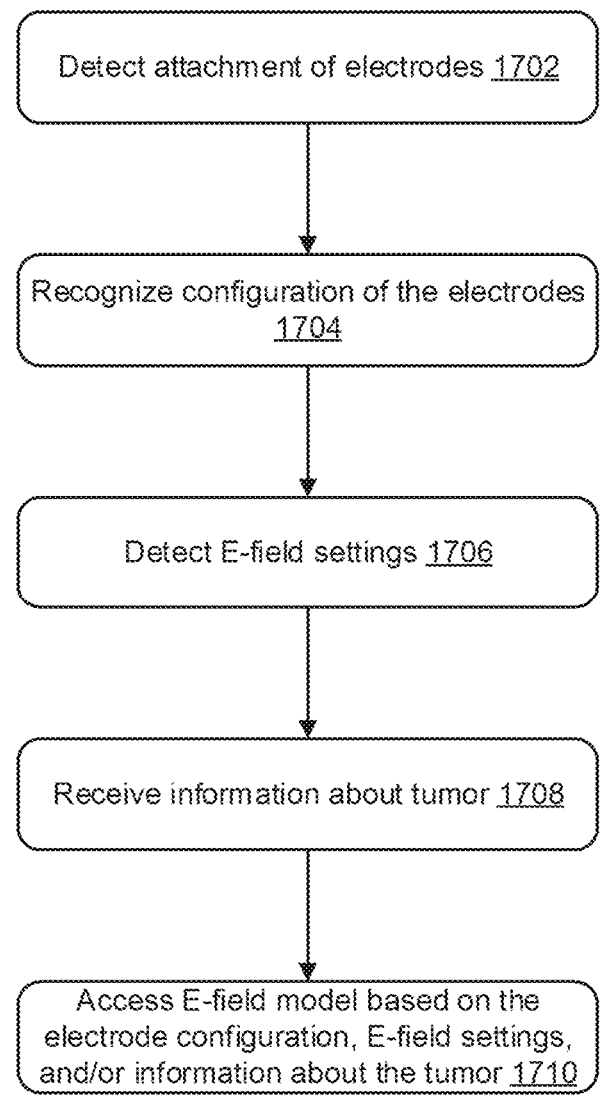
FIG. 17 illustrates a flow for accessing an electric field model in accordance with an embodiment.
Figure 18:
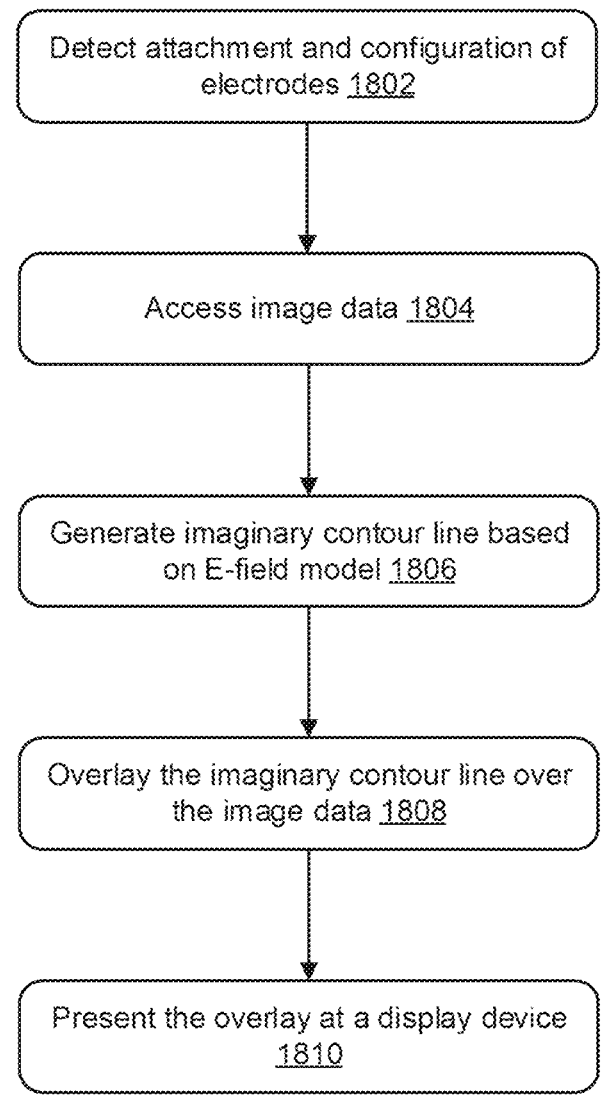
FIG. 18 illustrates a flow for presenting a visualization in accordance with an embodiment.
Figure 19:
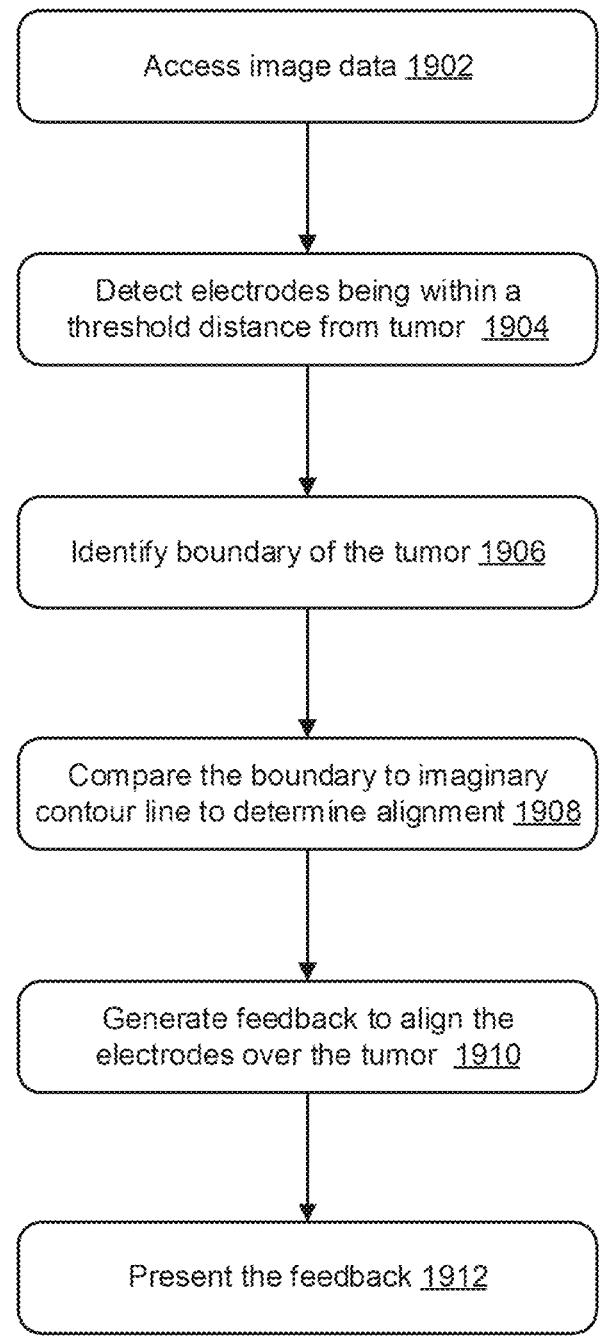
FIG. 19 illustrates a flow for presenting a visualization with feedback in accordance with an embodiment.

FIGS. 17-19 illustrate various flows that are implemented by components of the visualization system to generate and present the visualization.

Each of the illustrated operations of FIGS. 17-19 can be embodied in, and fully or partially automated, by applications executed by one or more processors and/or components of the visualization system. Additionally, while the operations are illustrated in a particular order, it should be understood that no particular order is necessary and that one or more operations may be omitted, skipped, and/or reordered.

FIG. 17 illustrates an example flow for accessing an electric field model. The visualization system uses the electric field model to generate the imaginary contour line. The example flow of FIG. 17 starts at operation 1702, where attachment of electrodes are detected. In an example, the operator attaches the electrodes to a plug-and-play interface of the delivery device. This interface includes a pinout. The visualization system detects the attachment based on activated pins of the pinout.

In alternative embodiments, the operator optionally inputs at a user interface (e.g., a keyboard, mouse, touch screen) data about the electrodes. The visualization system detects the attachment based on the operator input.

At operation 1704, a configuration of the electrodes is recognized. In an example, the visualization system recognizes the configuration from the activated pins. For instance, the activated pins are compared to a pinout table that maps pins to electrode configurations.

In another example, the visualization system recognizes the configuration from the operator input. For instance, the operator input identifies the configuration.

At operation 1706, the electric field settings are detected. Various detection techniques are available. In one example, the operator inputs power settings (e.g., amplitude, duration, and/or total number of electric pulses) at the pulse generator.

In another example, the operator additionally or alternatively inputs such settings at a computing system of the visualization system. In yet another example, the operator inputs the type and size of tumor at the computing system. In turn, the computing system stores a table that correlates electric field settings with treatment of the tumor given the type and size. Accordingly, the electric field settings are detected from the table based on the operator input.

At operation 1708, information about the tumor is received. This information includes the type and size of the tumor. In an example, the operator inputs such information at the user interface of the visualization system. Accordingly, the visualization system receives the information via the user interface. The information can also include information about an environment where the electric field is to be applied. For instance, the type of the tumor would indicate whether the electric field will be applied to a patient's skin or inside the patient's body. The type and/or size of the tumor would also indicate a geometry. As such, permittivity and geometry information can be derived from the type and size of the tumor and is usable to select a proper electric field model that accounts for the environment.

At operation 1710, an electric field model is accessed based on the electrode configuration, electric field settings, and/or information about the tumor. In an example, the visualization system stores different electric field models and a table that correlates the model that should be accessed to the electrode configuration, electric field settings, and/or information about the tumor (including, for instance, information about the environment). Accordingly, based on the recognized electrode configuration, detected electric field settings, and received tumor information, the visualization system selects and accesses the proper electric field model.

The visualization system uses the accesses electric field model to present a visualization that overlays the respective imaginary contour line over images of a camera device. FIG. 18 illustrates a flow for presenting the visualization.

The example flow of FIG. 18 starts at operation 1802, where attachment and configuration of electrodes are detected. This operation may be similar to operations 1702 and 1704 of FIG. 17. At operation 1804, where image data is accessed. In an example, the camera device generates and transmits the image data to the computing system of the visualization system. At operation 1806, the imaginary contour line is generated based on the electric field model. In an example, the electric field model includes data about the imaginary contour line. Accordingly, the visualization system generates the imaginary contour line from the electric field model.

At operation 1808, the imaginary contour line is overlaid over the image data. In an example, the visualization system generates a composite video from the image data and the imaginary contour line. At operation 1810, the overlay is presented at a display device. For example, the visualization system displays the composite video at the display device. The presented video provides a visualization of the overlay.

In addition to overlaying the imaginary contour line and the image data, the visualization also includes an overlay of the feedback relative to positioning the electrodes over the tumor. FIG. 19 illustrates a flow for presenting the feedback as part of the visualization.

The example flow of FIG. 19 starts at operation 1902, where the image data is accessed. At operation 1904, the electrodes are detected as being within a threshold distance from the tumor. The threshold distance represents a distance beyond which it is not necessary to provide the feedback. For instance, if the electrodes are too far from the tumor, no feedback is available or, if available, is inaccurate or meaningless. As soon as the electrodes are close enough to the tumor, the feedback becomes available and accurate. The threshold distance represents the balance between being too far and too close. In an example, the threshold distance is set as a function (e.g. a fraction) of the length of the electrodes. For example, if the electrodes are two inches long, the threshold distance is set as one inch.

Detecting that the electrodes are within the threshold distance includes determining that the ends of the electrodes that will contact the tumor are within that distance. Several detection techniques are available. In one example, the delivery device includes a rangefinder, such as a laser rangefinder. The rangefinder is configured to detect the distance between the ends of the electrode and the tumor. The visualization system compares this distance to the distance threshold to detect whether the ends are located within the threshold distance. In another example technique, no rangefinder is used. Instead, the image data is analyzed along with position, orientation, and acceleration data of the electrodes. For example, changes between sequential images are analyzed to determine the distance. The analysis uses image processing and geometric reconstruction to estimate the distance. Based on the position and orientation of the electrodes, a relative scale is determined in each of the images. Based on the determined scales and the acceleration of the electrodes, the changes between two images captured at different times are translated into the distance between the ends of the electrodes and the tumor.

At operation 1906, a boundary of the tumor is identified. In an example, the tumor is already fluorescently labeled. The camera device is capable of capturing the fluorescent light. The visualization system applies image processing and edge detection algorithms to detect the boundary from the image data.

At operation 1908, the boundary is compared to the imaginary contour line to determine an alignment (or misalignment as applicable) of the electrodes over the tumor. In an example, the visualization system compares the relative positions and/or orientation of the boundary and imaginary contour line. Any misalignment in position or orientation is detected and used to generate the feedback for aligning the electrodes over the tumor.

At operation 1910, the feedback to align the electrodes over the tumor is generated. In an example, the visualization system generates the feedback based on the misalignment in position or orientation. For instance, the feedback instructs the operator to move the electrodes in a certain direction along one axis (e.g., horizontal axis) to align the positions and along another axis (e.g., vertical axis) to align the orientations. At operation 1912, the feedback is presented. In an example, the visualization system displays the feedback at the display device as a set of instructions.

Autologous Vaccine

Figure 20:
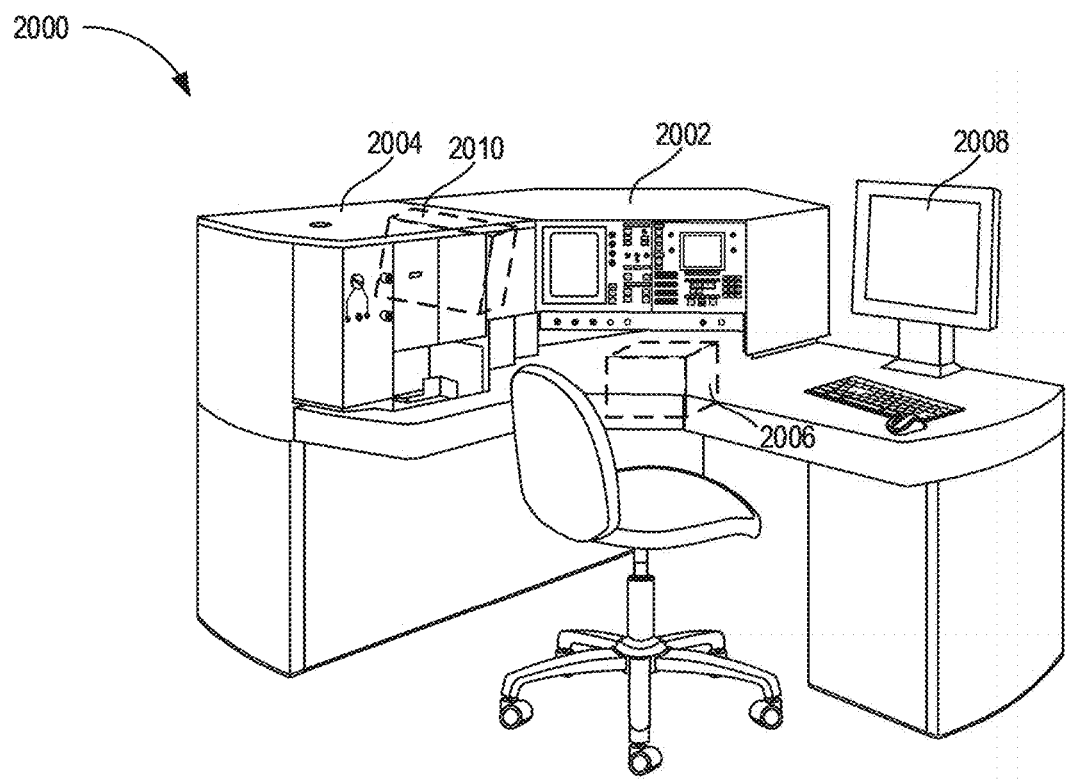
FIG. 20 illustrates an overall autologous vaccine system in accordance with an embodiment.

Turning to FIG. 20, the figure illustrates an autologous vaccine system 2000 in accordance with an embodiment. The example autologous vaccine system 2000 integrates a pulse generator 2002 and a flow cytometry system 2004, such as a fluorescence-activated cell sorting (FACS®), to generate a culture containing apoptotic tumor cells for injection into a subject as a vaccine. The autologous vaccine system 2000 includes a central controller 2006, such as a computer, for controlling the operations of the pulse generator 2002 and the flow cytometry system 2004. Additionally, the autologous vaccine system 2000 include a user interface 2008 that is connected to the central controller 2006. The user interface 2008 allows an operator to operate the autologous vaccine system 2000.

The pulse generator 2002 is configured to accept a container. A culture of cancerous cells is placed in the container. The pulse generator 2002 applies an electric field to the culture contained in the container. Settings of the electric including, for example, numbers of pulses, pulse widths and amplitudes, are inputted by the operator directly at the pulse generator 2002 or at the user interface 2008. In addition, the operator switches on and off the application of the electric field directly at the pulse generator 2002 or at the user interface 2008.

In an example, once the electric field application is complete, the culture is transferred from the container of the pulse generator 2002 to the flow cytometry system 2004 via an interface 2010 between the pulse generator 2002 and the flow cytometry system 2004. The interface 2010 can be, at least in part, mechanical and can include a transfer mechanism of the autologous vaccine system 2000. Different transfer mechanisms are available and can be operated automatically by the central controller 2006 and/or manually by the operator. In an example, the transfer mechanism (e.g., the interface 2010) includes a conduit and valves. The culture is accordingly transferred from the container of the pulse generator 2002 to another container (e.g., a cuvette) of the flow cytometry system 2004. In another example, the transfer mechanism (e.g., the interface 2010) includes a transfer arm (e.g., a robotic arm in the example of a central controller operation). Rather than transferring the culture between containers, the transfer arm transfers the container from the pulse generator 2002 to the flow cytometry system 2004.

Figure 21:
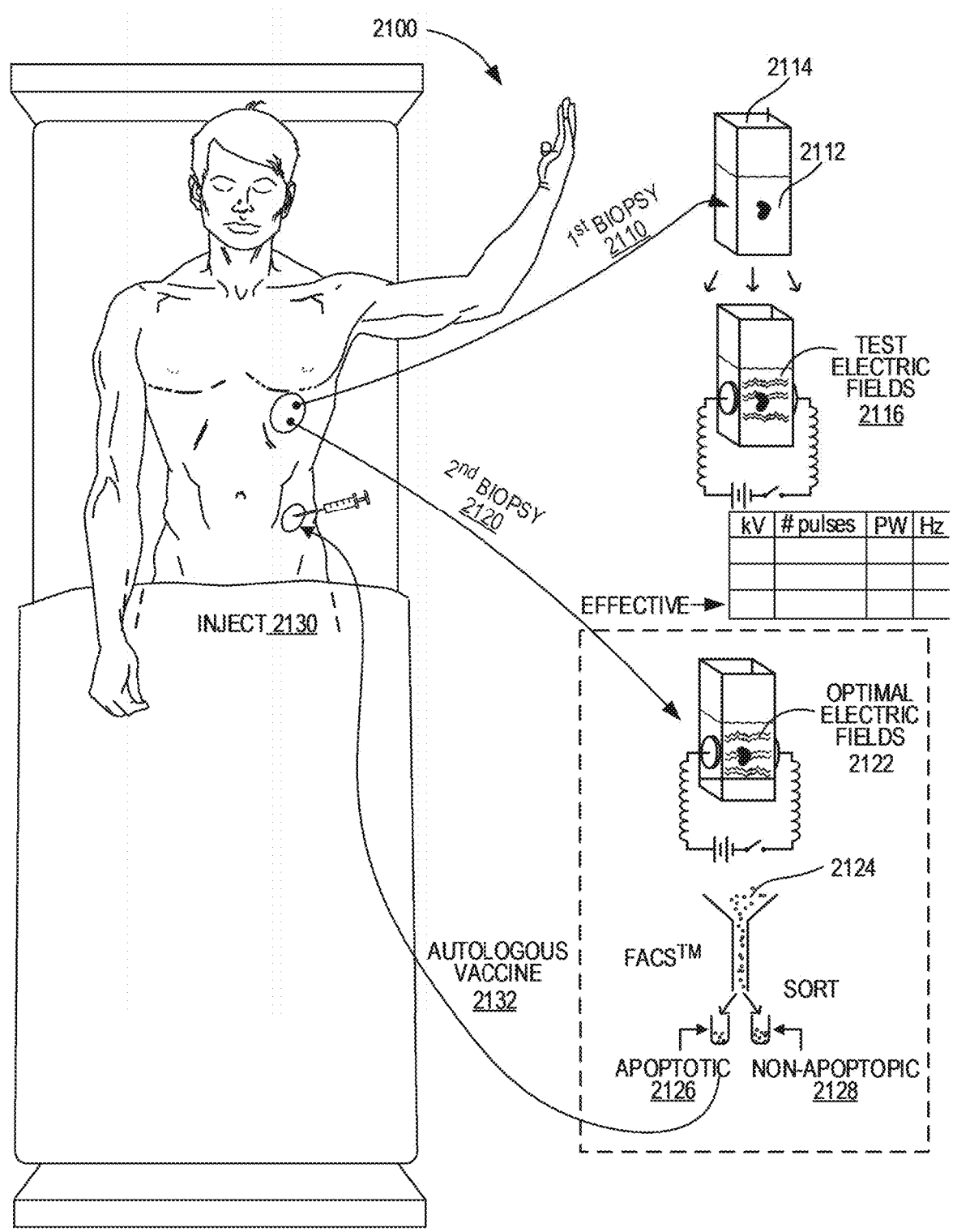
FIG. 21 illustrates an example autologous vaccine system in accordance with an embodiment.

FIG. 21 illustrates an autologous vaccine system 2100 in accordance with an embodiment. Components of the autologous vaccine system 2100 represent examples of some of the components of the autologous vaccine system 2000 of FIG. 20. In the autologous vaccine system 2100, a first biopsy 2110 of a cancerous tumor is conducted, and tumor cells are placed into a culture 2112 so that many separate experiments can be carried out on them exposed to a pulsed electric field in a cuvette 2114. The tumor cells are treated by way of multiple different treatments of nsPEF with different electrical parameters 2116. That is, different electric field intensities, numbers of pulses, pulse widths, and frequencies are tried on different cells from the biopsy. This is so that an effective treatment, maximizing apoptosis of the cells, can be formulated.

Apoptosis of cells can be detected by any of several techniques. One technique is to detect cleaved caspase-3 or cleaved caspase-9 within the cells. One can introduce a fluorescent label for cleaved caspase-3 or cleaved caspase-9 into the cells and then illuminate the cells so as to activate the fluorescence. The fluorescent cells, which are apoptotic (or necrotic), can then be separated from any non-apoptotic cells by using fluorescence-activated cell sorting (FACS®) or similar flow cytometry selection techniques.

Another exemplary technique to detect apoptosis of cells is to detect calreticulin on the outer surface walls of cells. One can introduce a fluorescent marker for calreticulin to the outer surface of the cell walls, and the antibody associated with the marker can bind with calreticulin. Fluorescence-activated cell sorting or similar techniques can then be used for separation. One can also introduce calreticulin antibodies connected with or to magnetic beads to the outer surface of the cell walls, and then a magnet can be applied to push or pull the calreticulin-expressing cells, which are apoptotic (or necrotic), to a separate container. Besides magnetic beads, other size and shape sorting techniques can be used.

Another technique for detecting apoptosis of cells is to detect pyknosis (shrinking of nuclei). Within two hours after nsPEF treatment, most cell nuclei shrink to about ½ their original sizes. A permeable dye can be introduced inside the cell, inside the nucleus, and label DNA (deoxyribonucleic acid) with an ultra-violet (UV)-activated fluorescent marker. The cells can be separated by imaging nuclei sizes and sorting using flow cytometry.

Yet another technique for detecting cell apoptosis is to detect cytochrome c release from mitochondria within the cell. An marker for cytochrome c is introduced within the cells, and the marker can be used similarly to the markers above for sorting and separation.

Other markers for detecting cell apoptosis include markers for molecules that change upon Immunogenic Cell Death (ICD). These molecules are sometimes referred to as Damage-Associated Molecular Pattern molecules (DAMPs).

DAMPS that are translocated to a cell surface or are released passively include:
 ATP (adenosine triphosphate)
 Calreticulin
 ERp57
 HSP70
 HSP90
 HSP60
 HSP72
 GRP78
 GP96
 HMGB1
 Reactive carbonyls and oxidation-specific epitopes
DAMPS that are moved through a secretory pathway for CRT/ERp57 include:
 PERK (protein kinase RNA-like endoplasmic reticulum kinase)
 BAX
 BAK
DAMPS that are moved through a secretory pathway for ATP include:
 PERK
 PI3K
Altered or mutated genes that are implicated in pathway components of DAMPS include:
 ATGS
 ATG7
 BECN1
 BCAP31
 Caspase 8
 P-eIF2a
 ERp57
 BAK1
 BAX
 EIF2AK3
 PIK3CA Once an effective or optimal nsPEF treatment is found, a second biopsy 2020 (which may be a portion of material from the first biopsy) is treated using electrical parameters 2122 of the effective/optimal nsPEF treatment. The resulting treated tumor cells 2124 are then sorted into those that exhibit sufficient apoptosis 2126 and those 2128 that do not. The treated, apoptotic tumor cells are then injected 2130 subdermally or intraperitoneally back into the same (or a different) subject as a vaccine 2132. In addition to the apoptotic tumor cells, a smaller amount of necrotic tumor cells can also be injected as part of the vaccine.

The vaccine can trigger an immune response in the subject, which directs CD8$^+$ cells or other immune responses against the original tumor and against any related secondary tumors elsewhere in the subject that were the result of metastasis.

Figure 22:
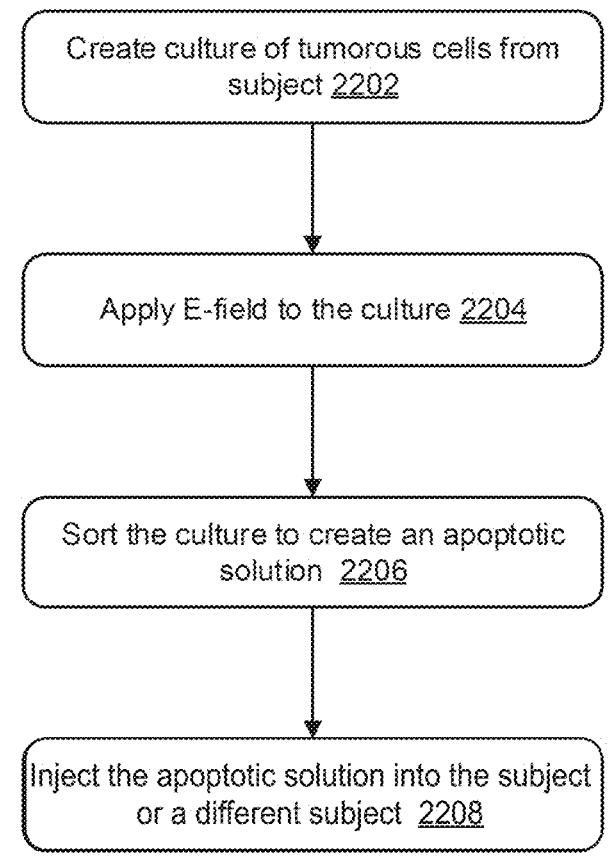
FIG. 22 illustrates a flow for injecting a vaccine in accordance with an embodiment.

FIG. 22 illustrates a flow for injecting a culture containing apoptotic tumor cells into a subject as a vaccine in accordance with an embodiment. The subject can be a human patient as illustrated in FIG. 21 or an animal (e.g., for experimentation). At operation 2202, a culture of tumorous cells is created from the subject. For example, an operator conducts a biopsy of the tumorous cells and places the tumorous cells into the culture. In turn, the culture is placed in a container of a pulse generator of an autologous vaccine system.

At operation 2204, an electric field is applied to the culture. In an example, the pulse generator applies a number of electric pulses having particular settings (e.g., pulse width, amplitude, number of pulses, and frequencies). The settings are derived from prior biopsy of the subject or biopsies of other subjects for the same type of tumor. For instance, the operator inputs an identifier of the subject and/or type of cancer. A central controller of the autologous vaccine system stores a table that identifies the settings given the identifier. In another illustrator, the operator inputs the settings directly at the pulse generator or at an interface of the autologous vaccine system.

At operation 2206, the culture is sorted to create an apoptotic solution. In an example, upon completion of the application of the electric field, the culture is transferred from the pulse generator to a flow cytometry system of the autologous vaccine system. For instance, the operator and/or the central controller performs the transfer. The flow cytometry system sorts the culture to create the apoptotic solution. Some amount of necrotic tumor cells can also be added to the apoptotic solution. Such an amount is smaller than the one of the apoptotic tumor cells.

At operation 2208, the apoptotic cell is injected back into the same or a different subject as a vaccine. The injection can be subdermal or intraperitoneal.

Technical advantages of this system and method include that no drugs are necessary, which often cause side effects and are nonlocal. Further, there is no requirement for synthesizing new compounds or their storage or distribution. Instead, a subject's own immune system is called to action by the autologous vaccination. The injection of tumor cells can be made in an area that is readily accessible to health care practitioners in order to more easily keep tabs on side effects. Perhaps most importantly, the system can work against metastasized tumors which have spread over so many areas of the body that it would be technically impossible to surgically remove. This may be especially important for fast-metastasizing tumors such as malignant melanomas or mesothelioma cancers that are difficult to detect until they are in later stages and have metastasized, such as lung cancer.

A rat orthotopic hepatocellular carcinoma model system has been used to show liver tumor ablation with nanosecond pulsed electric fields (nsPEF). NsPEF treatment can trigger apoptosis in rat liver tumor cells as evidenced by the appearance of cleaved caspase 3 and 9 within two hours after treatment. The growth of secondary tumors can be severely inhibited as compared to tumor growth in CD8-depleted rats. Nanoelectroablation can trigger immunogenic cell death, and thus it mediates the production of CD8$^+$ cytotoxic T-cells resulting in inhibition of tumor growth

What is claimed is:
1. A method of vaccinating a subject against a tumor, the method comprising
 passing multiple treatments of sub-microsecond pulsed electric fields with different parameters through tumor cells of a first subject;

selecting, based on the multiple treatments, optimized parameters to formulate an effective sub-microsecond pulsed electric fields treatment which increases or maximizes apoptosis of the tumor cells of the first subject; and using the formulated sub-microsecond pulsed electric fields treatment with the optimized parameters to create a vaccine with the increased or maximized apoptotic tumor cells to treat the tumor cells or other tumor cells of the first subject or a different subject with a same type of tumor cells.

2. The method of claim 1, wherein the passing multiple treatments is performed on different cells of the tumor cells, such that different electric field intensities, number of pulses, pulse widths, or frequencies are tried on the different cells of the tumor cells.

3. The method of claim 1, the method comprising storing the optimized parameters with an association to at least one of an identifier of the first subject or a type of the tumor cells.

4. The method of claim 1, wherein the passing multiple treatments is performed on the tumor cells extracted from the first subject.

5. The method of claim 4, wherein the step of using the formulated sub-microsecond pulsed electric fields treatment with the optimized parameters comprises reintroducing to the first subject at least a portion of the extracted tumor cells that has been treated with the optimized parameters.

6. The method of claim 4, wherein the step of using the formulated sub-microsecond pulsed electric fields treatment with the optimized parameters comprises applying the formulated sub-microsecond pulsed electric fields treatment with the optimized parameters to a second sample of tumor cells extracted from the first subject or to a sample extracted from the different subject with the same type of tumor cells.

7. The method of claim 1, wherein the sub-microsecond pulsed electric fields are pulsed at 100 ns pulse duration.

8. The method of claim 1, wherein the apoptosis of the tumor cells is detected using one or more of the following techniques: detecting cleaved caspase-3 or cleaved caspase-9 within treated tumor cells, detecting pyknosis, detecting calreticulin on outer surface walls of the tumor cells, detecting cytochrome c release from mitochondria within the tumor cells or Damage-Associated Molecular Pattern molecules (DAMPs).

9. The method of claim 1, wherein the tumor cells with the increased or maximized apoptosis are administered subdermally, intraperitoneally or into a bloodstream.

10. The method of claim 1, the method comprising detecting apoptotic tumor cells in the treated tumor cells by:
introducing a fluorescent label for cleaved caspase-3 or cleaved caspase-9 into the treated tumor cells;
illuminating the fluorescent label; and
separating the apoptotic tumor cells from the treated tumor cells based on the fluorescent label.

11. The method of claim 1, the method comprising detecting apoptotic tumor cells in the treated tumor cells by:
introducing calreticulin antibodies connected to magnetic beads to the treated tumor cells, the calreticulin antibodies binding with calreticulin on surfaces of the apoptotic tumor cells;
applying a magnet to the magnetic beads; and
separating the apoptotic tumor cells from the treated tumor cells based on the magnetic beads.

12. The method of claim 1, the method comprising detecting apoptotic tumor cells in the treated tumor cells by:
measuring a temperature increase of the tumor cells caused by the sub-microsecond pulsed electric fields; and
adjusting an intensity, pulse widths, or frequency of the sub-microsecond pulsed electric fields based on the measured temperature increase.

13. The method of claim 1, wherein at least the step of passing multiple treatments of sub-microsecond pulsed electric fields is performed using a device that stores instructions, that upon execution on the device, configure the device to at least perform the step.

14. The method of claim 1, wherein at least a portion of the sub-microsecond pulsed electric fields has an intensity greater than 10 kV/cm and pulse widths between 0.1 and 1000 nanoseconds.

15. The method of claim 1, the method comprising utilizing a user interface to input or select from stored options an identifier of the subject and/or a type of the tumor cells.

16. The method of claim 1, wherein the optimized parameters comprise one or more of the following: electric field intensities, number of pulses, amplitude, pulse widths, or frequencies.

17. The method of claim 1, the method comprising transferring the treated tumor cells from a pulse generator to a flow cytometry system.

18. The method of claim 1, the method comprising
generating the vaccine that includes apoptotic cells from the treated tumor cells.

19. The method of claim 18, wherein the vaccine is generated by further including necrotic tumor cells in the vaccine.

20. The method of claim 1, the method further comprising sorting the treated tumor cells between the apoptotic cells and non-apoptotic cells.

* * * * *